US012584110B2

(12) United States Patent
Lopez et al.

(10) Patent No.: US 12,584,110 B2
(45) Date of Patent: **\*Mar. 24, 2026**

(54) FUNCTIONAL FELINE PANCREATIC CELLS FROM ADIPOSE TISSUE

(71) Applicant: Board of Supervisors of Louisiana State University and Agriculture and Mechanical College, Baton Rouge, LA (US)

(72) Inventors: Mandi J. Lopez, St. Gabriel, LA (US); Wei Duan, Baton Rouge, LA (US)

(73) Assignee: BOARD OF SUPERVISORS OF LOUISIANA STATE UNIVERSITY AND AGRICULTURAL AND MECHANICAL COLLEGE, Baton Rouge, LA (US)

( \* ) Notice: Subject to any disclaimer, the term of this patent is extended or adjusted under 35 U.S.C. 154(b) by 111 days.

This patent is subject to a terminal disclaimer.

(21) Appl. No.: 18/371,839

(22) Filed: Sep. 22, 2023

(65) Prior Publication Data

US 2024/0124843 A1 Apr. 18, 2024

Related U.S. Application Data

(63) Continuation of application No. 16/307,777, filed as application No. PCT/US2017/055136 on Oct. 4, 2017, now Pat. No. 11,788,062.

(60) Provisional application No. 62/537,712, filed on Jul. 27, 2017.

(51) Int. Cl.
  *C12N 5/0775* (2010.01)
  *A61K 35/28* (2015.01)

(52) U.S. Cl.
  CPC ............ *C12N 5/0667* (2013.01); *A61K 35/28* (2013.01); *C12N 2500/33* (2013.01); *C12N 2500/38* (2013.01); *C12N 2501/115* (2013.01); *C12N 2501/12* (2013.01); *C12N 2501/16* (2013.01); *C12N 2501/33* (2013.01); *C12N 2501/335* (2013.01); *C12N 2501/345* (2013.01); *C12N 2501/39* (2013.01); *C12N 2501/998* (2013.01); *C12N 2501/999* (2013.01)

(58) Field of Classification Search
  CPC ................................................... C12N 5/0667
  See application file for complete search history.

(56) References Cited

U.S. PATENT DOCUMENTS

| | | | |
|---|---|---|---|
| 4,557,264 A | 12/1985 | Hinsch | |
| 5,567,612 A | 10/1996 | Vacanti et al. | |
| 5,759,830 A | 6/1998 | Vacanti et al. | |
| 5,770,417 A | 6/1998 | Vacanti et al. | |
| 6,022,743 A | 2/2000 | Naughton et al. | |
| 6,306,424 B1 | 10/2001 | Vyakarnam et al. | |
| 6,333,029 B1 | 12/2001 | Vyakamam et al. | |
| 6,365,149 B2 | 4/2002 | Vyakamam et al. | |
| 6,534,084 B1 | 3/2003 | Vyakamam et al. | |
| 6,599,323 B2 | 7/2003 | Melican et al. | |
| 6,626,950 B2 | 9/2003 | Brown et al. | |
| 6,656,488 B2 | 12/2003 | Yi et al. | |
| 7,029,915 B2 | 4/2006 | Yang | |
| 8,728,812 B2 | 5/2014 | Chen et al. | |
| 11,788,062 B2 * | 10/2023 | Lopez .................... | A61K 38/28 435/351 |
| 2003/0138951 A1 | 7/2003 | Yin | |
| 2004/0062753 A1 | 4/2004 | Rezania et al. | |
| 2011/0008301 A1 | 1/2011 | Trivedi et al. | |

FOREIGN PATENT DOCUMENTS

WO    2004-098646 A1    11/2004

OTHER PUBLICATIONS

Aksu et al., "Role of Gender and Anatomical Region on Induction of Osteogenic Differentiation of Human Adipose-derived Stem Cells", Annals of Plastic Surgery, Mar. 2008, vol. 60, No. 3, pp. 306-322.

Betsholtz et al., "Structure of Cat Islet Amyloid Polypeptide and Identification of Amino Acid Residues of Potential Significance for Islet Amyloid Formation", Diabetes, vol. 39, Jan. 1990, pp. 118-122.

Bloom et al., "Feline diabetes mellitus: clinical use of long-acting glargine and detemir", J Feline Med Surg., (Mar. 2014); 16(3): 205-15.

Buang et al., "In vitro Generation of Functional Insulin-producing Cells from Lipoaspirated Human Adipose Tissue-derived Stem Cells", Archives of Medical Research, 2012, vol. 43, pp. 83-88.

Chance et al., "Porcine Proinsulin: Characterization and Amino Acid Sequence", Science, New Series, Jul. 12, 1968, vol. 161, No. 3837, pp. 165-167.

Chandra et al., "Generation of Pancreatic Hormone-Expressing Islet-Like Cell Aggregates from Murine Adipose Tissue-Derived Stem Cells", Stem Cells, vol. 27, 2009, pp. 1941-1953.

Chandra et al., "Islet-Like Cell Aggregates Generated from Human Adipose Tissue Derived Stem Cells Ameliorate Experimental Diabetes in Mice", PLoS ONE, vol. 6, Issue 6, e20615, Jun. 7, 2011, pp. 1-12.

(Continued)

*Primary Examiner* — Anoop K Singh
*Assistant Examiner* — David A Montanari
(74) *Attorney, Agent, or Firm* — Venable LLP; Keith G. Haddaway; Hemant Khanna

(57) ABSTRACT

Compositions and methods are described herein for transdifferentiation of multipotent stromal cells into cells that can express insulin.

6 Claims, 20 Drawing Sheets

Specification includes a Sequence Listing.

(56) References Cited

OTHER PUBLICATIONS

Chen et al., "Differentiation of rat marrow mesenchymal stem cells into pancreatic islet beta-cells," World Journal of Gastroenterology, vol. 10, No. 20, 2004, pp. 3016-3020.

Chen et al., "MicroRNAs Modulate Hematopoietic Lineage Differentiation," Science, vol. 303, No. 5654, 2004, pp. 83-86.

Clark et al. "Human and feline adipose-derived mesenchymal stem cells have comparable phenotype, immunomodulatory functions, and transcriptome", Stem Cell Res Ther., (Mar. 2, 20170); 8(1):69.

Dahan et al., "Pancreatic ?- Cells Express the Fetal Islet Hormone Gastrin in Rodent and Human Diabetes", Diabetes, (Feb. 1, 2017), vol. 66, No. 2, pp. 426-436.

D'Amour et al., "Production of pancreatic hormone-expressing endocrine cells from human embryonic stem cells", Nature Biotech., vol. 24, No. 11, 2006, pp. 1392-1401.

Dang et al., "Production of islet-like insulin-producing cell clusters in vitro from adipose-derived stem cells", Biomedical Research and Therapy, 2015, vol. 2, No. 1, pp. 184-192.

Dave et al., "Extrinsic Factors Promoting In Vitro Differentiation of Insulin-Secreting Cells from Human Adipose Tissue-Derived Mesenchymal Stem Cells", Appl Biochem Biotechnol, 2013, vol. 170, pp. 962-971.

Dominici et al., "Minimal criteria for defining multipotent mesenchymal stomal cells. The International Society for Cellular Therapy position statement", Cytotherapy, 2006, vol. 8, No. 4, pp. 315-317.

Drummond et al., "Clinical Development of Histone Deacetylase Inhibitors as Anticancer Agents", Annu. Rev. Pharmacol. Toxicol., vol. 45, 2005, pp. 495-528.

Dubey et al., "198 Isolation, Characterization and in Vitro Differentiation of Goat Adipose-Tissue-Derived Mesenchymal Stem Cells Into Pancreatic Islets-Like Cells", Reproduction, Fertility and Development, vol. 26, 2014, p. 213.

Efrat, "Generation of Insulin-Producing Cells from Stem Cells for Cell Replacement Therapy of Type 1 Diabetes", IMAJ, May 2004, vol. 6, pp. 265-267.

Evans et al., "Are Oxidative Stress-Activated Signaling Pathways Mediators of Insulin Resistance and b-Cell Dysfunction?", Diabetes, vol. 52, 2003, pp. 1-8.

Fargason et al., Feline Adult Adipose Tissue-Derived Multipotent Stromal Cell Isolation and Differentiation. In: Bunnell B.A., Gimble J.M. (eds) Adipose-Derived Stem Cells, Methods in Molecular Biology, (2018), vol. 1773. Humana Press, New York, NY. <https://doi.org/10.1007/978-1-4939-7799-4_15> [Abstract Only].

Fu et al., "Regulation of Insulin Synthesis and Secretion and Pancreatic Beta-Cell Dysfunction in Diabetes", Current Diabetes Reviews, vol. 9, 2013, pp. 25-53.

Goosens et al., "Response to Insulin Treatment and Survival in 104 cats with Diabetes Mellitus (1985-1995)", Journal of Veterinary Internal Medicine, vol. 12, 1998, pp. 1-6.

International Search Report issued by the World Intellectual Property Organization in International Application No. PCT/US2017/055136, dated Feb. 9, 2018.

Janjic et al., "Effect of 2-mercaptoethanol on gluthathione levels, cystine uptake and insulin secretion in insulin-secreting cells", European Journal of Biochemistry, vol. 210, 1992, 297-304.

Kono et al., "Phenotypic and functional properties of feline dedifferentiated fat cells and adipose-derived stem cells", The Veterinary Journal, 2014, vol. 199, pp. 88-96.

Liu et al., "Cryopreservation of Human Bone Marrow-Derived Mesenchymal Stem Cells with Reduced Dimethylsulfoxide and Well-Defined Freezing Solutions", Biotechnology progress, vol. 26, No. 6, 2010, pp. 1635-1643.

Lopez et al., "State of the art: stem cells in equine regenerative medicine", Equine Veterinary Journal, vol. 47, 2015, pp. 145-154.

McCann et al., "Feline diabetes mellitus in the UK: the prevalence within an insured cat population and a questionnaire-based putative risk factor analysis", Journal of Feline Medicine and Surgery, 2007, vol. 9, pp. 289-299.

McIntosh et al., "Immunogenicity of Allogeneic Adipose-Derived Stem Cells in a Rat Spinal Fusion Model", Tissue Engineering: Part A, (2009), vol. 15, No. 9, pp. 2677-2686, doi: 10.1089/ten.TEA.2008.0566.

Merani et al., "Optimal implantation site for pancreatic islet transplantation", Br J Surg., (Dec. 2008), 95 (12):1449-61.

Mizisin et al., "Neurological Complications Associated with Spontaneously Occurring Feline Diabetes Mellitus." Journal of Neuropathology & Experimental Neurology, vol. 61, No. 10, 2002, pp. 872-884.

Moshtagh et al., "Differentiation of human adipose-derived mesenchymal stem cell into insulin-producing cells: an in vitro study", J Physiol Biochem, 2013, vol. 69, pp. 451-458.

Nayak et al., "Autologous and Allogenous Antibodies in Lung and Islet Cell Transplantation", Front Immunol., (Dec. 2016), 23;7:650.

Niclauss et al.,"Rapamycin impairs proliferation of transplanted islet f3 cells", Transplantation., (Apr. 2011), 15; 91(7):714-22.

O'Brien, "Pathogenesis of feline diabetes mellitus", Molecular and Cellular Endocrinology, 2002, vol. 197, pp. 213-219.

Okura et al., "Transdifferentiation of human adipose tissue-derived stomal cells into insulin-producing clusters", J Artif Organs, 2009, vol. 12, pp. 123-130.

Panciera et al., "Epizootiologic paterns of diabetes mellitus in cats: 333 cases (1980-1986)", Journal of the American Veterinary Medical Association, (1990), vol. 197, Iss. 11, pp. 1504-1508.

Pepper et al., "Current status of clinical islet transplantation", World J Transplant., (2013), 3(4):48-53.

Phillips et al., "Activin and related proteins in inflammation: Not just interested bystanders", Cytokine Growth Factor Rev., vol. 20, Issue 2, 2009, pp. 153-164.

Pokrywczynska et al., "Differentiation of Stem Cells into Insulin-Producing Cells: Current Status and Challenges," Arch. Immunol. Ther. Exp., vol. 61, 2013, 149-158.

Polak et al., "Early Pattern of Differentiation in the Human Pancreas," Diabetes, vol. 49, 2000, pp. 225-232.

Prahl et al., "Time trends and risk factors for diabetes mellitus in cats presented to veterinary teaching hospitals", Journal of Feline Medicine and Surgery, 2007, vol. 9, pp. 351-358.

Rand et al., "Canine and feline Diabetes Mellitus: Nature or Nurture?" J. Nutrition, vol. 134, 2004, 2072S-2080S.

Russ et al., "Insulin-producing cells generated from dedifferentiated human pancreatic beta cells expanded in vitro", PLoS One. (2011);6(9): e25566.

Ryan et al., "Five-Year Follow-Up After Clinical Islet Transplantation," Diabetes, vol. 54, 2005, pp. 2060-2069.

Sander et al., "Genetic analysis reveals that PAX6 is required for normal transcription of pancreatic hormone genes and islet development," Genes & Development, 1997, vol. 11, pp. 1662-1673.

Schwartz, "Diabetes Mellitus: Does it Affect Bone?", Calcifi Tissue Int, 2003, vol. 73, pp. 515-519.

Shapiro et al. "Islet Transplantation in Seven Patients With Type 1 Diabetes Mellitus Using a Glucocorticoid-Free Immunosuppressive Regimen" New England Journal of Medicine, Jul. 27, 2000, vol. 343, No. 4, pp. 230-238.

Shehadeh et al., "Cardiac Consequences of Diabetes Mellitus", Clin, Cardiol., vol. 18, 1995, pp. 301-305.

Sigmundsson et al., "Culturing functional pancreatic islets on ?5-laminins and curative transplantation to diabetic mice", Matrix Biology, (2018), vol. 70, pp. 5-19.

Sittinger et al., "Current strategies for cell delivery in cartilage and bone regeneration", Current Opinion in Biotechnology, 2004, vol. 15, pp. 411-418.

Vaca et al., "Nicotinamide Induces Both Proliferation and Differentiation of Embryonic Stem Cells Into Insulin-Producing Cells", Transplantation Proceedings, 2003, vol. 35, pp. 2021-2023.

Van der Valk et al., "The humane collection of fetal bovine serum and possibilites for serum-free cell and tissue culture", Toxicology in Vitro, vol. 18, 2004, 1-12.

Webb et al., "In vitro comparison of feline bone marrow-derived and adiposse tissue-derived mesenchymal stem cells," Journal of Feline Medicine and Surgery, vol. 14, No. 2, 2012, pp. 165-168.

Werner et al., "Roles of activin in tissue repair, fibrosis, and inflammatory disease", Cytokine Growth Factor Rev., vol. 17, Issue: 3, 2006, pp. 157-171.

(56)        References Cited

OTHER PUBLICATIONS

Zhang et al., "The challenges and promises of allogeneic mesenchymal stem cells for use as a cell-based therapy", Stem Cell Res Ther., (Dec. 2015), 1;6:234.

Zhang et al., "Therapeutic Doses of Multipotent Stromal Cells from Minimal Adipose Tissue," Stem Cell Reviews and Reports, vol. 10, 2014, pp. 600-611.

* cited by examiner

```
SEQUENCE LISTING

Sequence total quantity: 24
SEQ ID NO: 1            moltype = DNA  length = 20
FEATURE                 Location/Qualifiers
source                  1..20
                        mol_type = other DNA
                        organism = synthetic construct
SEQUENCE: 1
agccttcctt cctgggtatg                                        20

SEQ ID NO: 2            moltype = DNA  length = 20
FEATURE                 Location/Qualifiers
source                  1..20
                        mol_type = other DNA
                        organism = synthetic construct
SEQUENCE: 2
acagcaccgt gttagcgtag                                        20

SEQ ID NO: 3            moltype = DNA  length = 17
FEATURE                 Location/Qualifiers
source                  1..17
                        mol_type = other DNA
                        organism = synthetic construct
SEQUENCE: 3
aacgaaatac ttggcgg                                           17

SEQ ID NO: 4            moltype = DNA  length = 20
FEATURE                 Location/Qualifiers
source                  1..20
                        mol_type = other DNA
                        organism = synthetic construct
SEQUENCE: 4
```

-continued

```
ccagaggctt gttgtagtcg                                              20

SEQ ID NO: 5              moltype = DNA   length = 18
FEATURE                   Location/Qualifiers
source                    1..18
                          mol_type = other DNA
                          organism = synthetic construct
SEQUENCE: 5
ggcaatcggt ggtagtaa                                                18

SEQ ID NO: 6              moltype = DNA   length = 19
FEATURE                   Location/Qualifiers
source                    1..19
                          mol_type = other DNA
                          organism = synthetic construct
SEQUENCE: 6
cttggtatgt tatcgttgg                                               19

SEQ ID NO: 7              moltype = DNA   length = 18
FEATURE                   Location/Qualifiers
source                    1..18
                          mol_type = other DNA
                          organism = synthetic construct
SEQUENCE: 7
caaggacaag aagcggag                                                18

SEQ ID NO: 8              moltype = DNA   length = 18
FEATURE                   Location/Qualifiers
source                    1..18
                          mol_type = other DNA
                          organism = synthetic construct
SEQUENCE: 8
ctgggtttgc ctgtaagc                                                18

SEQ ID NO: 9              moltype = DNA   length = 19
FEATURE                   Location/Qualifiers
source                    1..19
                          mol_type = other DNA
                          organism = synthetic construct
SEQUENCE: 9
ttggcttgga tgagttacg                                               19

SEQ ID NO: 10             moltype = DNA   length = 19
FEATURE                   Location/Qualifiers
source                    1..19
                          mol_type = other DNA
                          organism = synthetic construct
SEQUENCE: 10
gactttcctt tggtttccg                                               19

SEQ ID NO: 11             moltype = DNA   length = 17
FEATURE                   Location/Qualifiers
source                    1..17
                          mol_type = other DNA
                          organism = synthetic construct
SEQUENCE: 11
cttcgtcaac cagcacc                                                 17

SEQ ID NO: 12             moltype = DNA   length = 17
FEATURE                   Location/Qualifiers
source                    1..17
                          mol_type = other DNA
                          organism = synthetic construct
SEQUENCE: 12
acagcattgc tccacga                                                 17

SEQ ID NO: 13             moltype = DNA   length = 19
FEATURE                   Location/Qualifiers
source                    1..19
                          mol_type = other DNA
                          organism = synthetic construct
SEQUENCE: 13
tgaacaccaa gaggaacaa                                               19

SEQ ID NO: 14             moltype = DNA   length = 18
FEATURE                   Location/Qualifiers
source                    1..18
                          mol_type = other DNA
                          organism = synthetic construct
```

-continued

```
SEQUENCE: 14
accagccaag caatgaat                                                18

SEQ ID NO: 15           moltype = DNA   length = 19
FEATURE                 Location/Qualifiers
source                  1..19
                        mol_type = other DNA
                        organism = synthetic construct
SEQUENCE: 15
ccagacagag aacgatgcc                                               19

SEQ ID NO: 16           moltype = DNA   length = 19
FEATURE                 Location/Qualifiers
source                  1..19
                        mol_type = other DNA
                        organism = synthetic construct
SEQUENCE: 16
cagggtttga gttagtgga                                               19

SEQ ID NO: 17           moltype = DNA   length = 20
FEATURE                 Location/Qualifiers
source                  1..20
                        mol_type = other DNA
                        organism = synthetic construct
SEQUENCE: 17
aacaacagcc tctactacag                                              20

SEQ ID NO: 18           moltype = DNA   length = 18
FEATURE                 Location/Qualifiers
source                  1..18
                        mol_type = other DNA
                        organism = synthetic construct
SEQUENCE: 18
tatcctccga ccgaatcc                                                18

SEQ ID NO: 19           moltype = DNA   length = 19
FEATURE                 Location/Qualifiers
source                  1..19
                        mol_type = other DNA
                        organism = synthetic construct
SEQUENCE: 19
ccaacacctt catcatccg                                               19

SEQ ID NO: 20           moltype = DNA   length = 19
FEATURE                 Location/Qualifiers
source                  1..19
                        mol_type = other DNA
                        organism = synthetic construct
SEQUENCE: 20
ccatcatttc ctcctcctg                                               19

SEQ ID NO: 21           moltype = DNA   length = 19
FEATURE                 Location/Qualifiers
source                  1..19
                        mol_type = other DNA
                        organism = synthetic construct
SEQUENCE: 21
acagacaaga ggtttcagc                                               19

SEQ ID NO: 22           moltype = DNA   length = 19
FEATURE                 Location/Qualifiers
source                  1..19
                        mol_type = other DNA
                        organism = synthetic construct
SEQUENCE: 22
tatgaccgtg tgatggaac                                               19

SEQ ID NO: 23           moltype = DNA   length = 19
FEATURE                 Location/Qualifiers
source                  1..19
                        mol_type = other DNA
                        organism = synthetic construct
SEQUENCE: 23
tgagaagatg gtgagtggc                                               19

SEQ ID NO: 24           moltype = DNA   length = 18
FEATURE                 Location/Qualifiers
source                  1..18
                        mol_type = other DNA
```

-continued

```
                    organism = synthetic construct
SEQUENCE: 24
ggcagagcga aatgagac                                              18
```

1

FUNCTIONAL FELINE PANCREATIC CELLS FROM ADIPOSE TISSUE

PRIORITY

This application is a continuation of U.S. application Ser. No. 16/307,777, filed Dec. 6, 2018, which is a national stage application of PCT/US2017/055136, filed on Oct. 4, 2017, which claims benefit of the priority filing date of U.S. Provisional Patent Application Ser. No. 62/537,712, filed Jul. 27, 2017, the contents of all of which are specifically incorporated by reference herein in their entirety.

SEQUENCE LISTING

The instant application contains a Sequence Listing which has been submitted electronically in XML format and is hereby incorporated by reference in its entirety. Said XML copy, created on Dec. 19, 2023, is named 144240 580603.xml and is 22,267 bytes in size.

BACKGROUND

Diabetes mellitus is one of the most prevalent feline endocrinopathies. About 15-20% of feline diabetes cases are caused by decreased β-cell numbers or insulin resistance (Rand et al., J Nutrition 134:1072S-1080S (2004); Sittinger et al. Curr. Opin. Biotech. 15:411-418 (2004)). The condition affects all breeds and sexes and is associated with reproductive sterilization[5,6], obesity, physical inactivity[7], and advancing age[8] and drug side effects (McCann et al., J. Feline Med & Surg 9: 289-299 (2007); Pancciera et al., J Am Vet Med Assoc 197: 1504-1508 (1990); Prahl et al., J. Feline Med & Surg 9: 351-358 (2007); O'Brien, Molec Cell Endocrinol 197: 213-219 (2002)). To date, no single cause or effective cure has been identified.

Serious complications associated with unregulated glucose levels include increased bone fractures, cardiovascular disease, and neurological dysfunction, among others (Schwartz Calcified Tissue Internat 73:515-519 (2003); Shehadeh & Regan, Clin. Cardiol. 18: 301-305 (1995); Mizisin et al., J Neuropath & Exp. Neurol. 61-872-884 (2002)). Contemporary treatment consists of diet and weight management with exogenous insulin administration to replace that normally produced by pancreatic β cells (Fu et al., Curr. Diabetes Rev. 9: 25 (2013)). Available insulin formulations do not share the feline amino acid sequence. Though insulin maintains biological activity across species, sequence differences may affect activity and stimulate the immune system (Betsholtz et al., Diabetes 39: 118-122 (1990); Chance et sl., Science 161: 165-167 (1968)). Additionally, insulin administration is typically customized for individual patients, a challenging and time-consuming process. The time and costs associated with establishing and revising insulin therapy and daily injections can be a burden on the owners.

SUMMARY

Methods and compositions are described herein for transdifferentiation of feline starting cells such as adipose-derived multipotent stromal cells (ASCs) to generate pancreatic β cells. Such starting cells (e.g., ASCs) can be obtained from adipose tissues, for example, from subcutaneous adipose tissue or from reproductive organs (e.g., when they are removed during routine feline sterilization procedures). Results are described herein that quantify the transdifferentiation capability of feline starting cells such as ASCs. The feline starting cells cultured in pancreatic β cell induction medium had better insulin production and glucose response compared to that cultured in stromal medium.

One method described to generate pancreatic 3 cells can include:

a. Stage 1: culturing adult adipose-derived multipotent stromal (stem) cells (ASCs) for about 1-4 days in a first culture medium comprising insulin-transferrin-selenium, activin A, sodium butyrate, and 2-mercapethanol to generate a first population of cells that express at least one of the following genes: Nkx 6.1, Pax6, Isl1, or Glut-2;

b. Stage 2: culturing the first population of cells for 4 to 8 days in a second culture medium comprising insulin-transferrin-selenium, and taurine to generate a second population of cells; and c. Stage 3: culturing the second population of cells for 2 to 6 days in a third culture medium comprising insulin-transferrin-selenium, taurine, glucagon-like peptide 1 (GLP-1), nicotinamide, pentagastrin, and betacellulin to generate a third population of cells.

Cells in the second population typically express Nkx 6.1, Pax6, Isl1, and/or Glut-2 at greater expression levels than cells in the first population. Cells in the third population also typically express Nkx 6.1, Pax6, Isl1, and/or Glut-2 at greater expression levels than cells in the second population.

The methods can also include administering the third population of cells (or a portion thereof) to a subject, for example, a feline subject.

In some cases, the first culture medium, the second culture medium, and the third culture medium can further include at least one, at least two, at least three, or at least four of the following: basic fibroblast growth factor (bFGF), hepatocyte growth factor (HGF), laminin, N-2 supplement, or B-27 supplement.

In some cases the first culture medium, the second culture medium, and the third culture medium can also contain glucose, and/or serum albumin (e.g., bovine serum albumin).

Cells in the second population of cells and/or the third population of cells can express insulin. However, cells in the first population of cells typically do not express detectable amounts of insulin mRNA as detected by quantitative polymerase chain polymerase reaction.

Compositions are also described herein.

For example, one type of cell composition can include a first population of cells made by: culturing adult adipose-derived multipotent stromal (stem) cells (ASCs) from feline adipose tissue for about 1-4 days in a first culture medium comprising insulin-transferrin-selenium, activin A, sodium butyrate, and 2-mercapethanol to generate a first population of cells that express at least one of the following genes: Nkx 6.1, Pax6, Isl1, or Glut-2.

Another type of cell composition can include a second population of cells made by:

a. Stage 1: culturing adult adipose-derived multipotent stromal (stem) cells (ASCs) for about 1-4 days in a first culture medium comprising insulin-transferrin-selenium, activin A, sodium butyrate, and 2-mercapethanol to generate a first population of cells that express at least one of the following genes: Nkx 6.1, Pax6, Isl1, or Glut-2; and b. Stage 2: culturing the first population of cells for 4 to 8 days in a second culture medium comprising insulin-transferrin-selenium, and taurine to generate a second population of cells.

Another type of cell composition can include a third population of cells made by:

a. Stage 1: culturing adult adipose-derived multipotent stromal (stem) cells (ASCs) for about 1-4 days in a first culture medium comprising insulin-transferrin-selenium, activin A, sodium butyrate, and 2-mercapethanol to generate a first population of cells that express at least one of the following genes: Nkx 6.1, Pax6, Isl1, or Glut-2;

b. Stage 2: culturing the first population of cells for 4 to 8 days in a second culture medium comprising insulin-transferrin-selenium, and taurine to generate a second population of cells; and c. Stage 3: culturing the second population of cells for 2 to 6 days in a third culture medium comprising insulin-transferrin-selenium, taurine, glucagon-like peptide 1 (GLP-1), nicotinamide, pentagastrin, and betacellulin to generate a third population of cells.

Composition are also included herein that are useful for transdifferentiation of cells. Such compositions can be formulated as a culture medium, or as a dry composition or a concentrated liquid that is later rehydrated or diluted, respectively, to generate the culture medium.

For example, one type of composition can include at least four, or at least five, or at least six, or at least seven, or at least eight, or at least nine, or at least ten of the following: glucose, bovine serum albumin, insulin-transferrin-selenium, activin A, sodium butyrate, 2-mercapethanol, N-2 supplement, B-27 supplement, laminin, hepatocyte growth factor (HGF), or basic fibroblast growth factor (bFGF).

Another type of composition can include at least four, or at least five, or at least six, or at least seven, or at least eight of the following: glucose, bovine serum albumin, insulin-transferrin-selenium, taurine, laminin, basic fibroblast growth factor (bFGF), N-2 supplement, B-27 supplement, or human hepatocyte growth factor (HGF).

Another type of composition can include at least four, or at least five, or at least six, or at least seven, or at least eight, or at least nine, or at least ten, or at least eleven, or at least twelve of the following: glucose, bovine serum albumin, insulin-transferrin-selenium, taurine, glucagon-like peptide 1 (GLP-1), nicotinamide, non-essential amino acids, pentagastrin, N-2 supplement, B-27 supplement, human hepatocyte growth factor (HGF), basic fibroblast growth factor (bFGF), laminin, or betacellulin.

DESCRIPTION OF THE FIGURES

FIG. 1A is a photomicrograph showing ASCs after culturing in stromal medium. The scale is a 5× scale, and the scale bar=500 μm. FIG. 1B is a photomicrograph showing alizarin red stained ASCs after culturing in osteogenic medium. The scale is a 5× scale, and the scale bar=500 μm. Alizarin red staining illustrates calcium deposition. FIG. 1C is a photomicrograph showing oil red O lipid stained ASCs after culture in adipogenic medium. The scale is a 40× scale, and the scale bar=50 μm.

FIG. 2A shows a light photomicrograph of fresh male feline P3 ASCs cultured in stromal medium. FIG. 2B shows a light photomicrograph of fresh male feline P3 ASCs cultured in pancreatic β-cell induction medium and transferred to the normal culture plate. FIG. 2C shows a light photomicrograph of fresh female feline P3 ASCs cultured in pancreatic β-cell induction medium and transferred to the normal culture plate. 5× magnification. Scale bar=500 μm.

FIG. 3A shows a light photomicrograph of fresh male feline P3 ASCs stained with dithizone cultured in stromal medium. FIG. 3B shows a light photomicrograph of fresh male feline P3 dithizone-stained ASCs cultured in pancreatic 3-cell induction medium. FIG. 3C shows a light photomicrograph of fresh female feline P3 dithizone-stained ASCs cultured in pancreatic β-cell induction medium. Dithizone binds zinc ions present in the islet's beta cells, and therefore stains the islets. 20× magnification, scale bar=100 μm (A, B); 40× magnification, scale bar=50 μm.

FIG. 6A illustrates a transmission electron photomicrograph of feline ASCs cultured in stromal medium. FIG. 6B illustrates a transmission electron photomicrograph of feline ASCs cultured in induction medium. Legend: M—mitochondria, G—secretory granules. Scale bar=2 μm.

FIG. 7A shows transmission electron photomicrographs of feline ASCs cultured in stromal medium. FIG. 7B shows transmission electron photomicrographs of feline ASCs cultured in β cell induction medium. Scale bar=0.5 μm.

FIG. 8A shows scanning electron photomicrographs of feline ASCs cultured in stromal medium. FIG. 8B shows scanning electron photomicrographs of feline ASCs cultured in β cell induction medium. White arrows illustrate cell cluster morphology. Black arrows illustrate proteinaceous material on the surface of clusters cultured in induction medium. Scale bar=5 μm.

FIG. 9A graphically illustrates expression of feline NK6 homeobox 1 (NK6.1) in feline ASCs following three stages of pancreatic β cell culture induction. FIG. 9B graphically illustrates expression of feline paired box 6 (Pax6) in feline ASCs following three stages of pancreatic β cell culture induction. FIG. 9C graphically illustrates expression of feline ISL LIM homeobox 1 (Isl1) in feline ASCs following three stages of pancreatic β cell culture induction. FIG. 9D graphically illustrates expression of feline glucose transporter 2 (Glut2) in feline ASCs following three stages of pancreatic β cell culture induction. Expression levels (LS mean±SEM) are shown. Columns with distinct superscripts are significantly different between sexes within stages. Different asterisk numbers (*) are significantly different among stages within gender.

FIG. 10A graphically illustrates expression of feline insulin in feline ASCs following three stages of pancreatic β cell culture induction. FIG. 10B graphically illustrates expression of feline glucagon in feline ASCs following three stages of pancreatic β cell culture induction. FIG. 10C graphically illustrates expression of feline somatostatin in feline ASCs following three stages of pancreatic β cell culture induction. Expression levels (LS mean±SEM) are shown. Columns with different asterisk numbers (*) are significantly different among stages within gender.

FIG. 11A graphically illustrates expression of feline proto-oncogene tyrosine-protein kinase ROS1 in feline ASCs following three stages of pancreatic β cell culture induction. FIG. 11B graphically illustrates expression of feline serine/threonine kinase 1 AKT1 in feline ASCs following three stages of pancreatic β cell culture induction. FIG. 11C graphically illustrates expression of feline Ras-related protein RAB2A in feline ASCs following three stages of pancreatic β cell culture induction. FIG. 11D graphically illustrates expression of feline hexokinase 1 HK1 in feline ASCs following three stages of pancreatic β cell culture induction. Expression levels (LS mean±SEM) are shown.

DETAILED DESCRIPTION

Figures 1A, 1B, 1C:
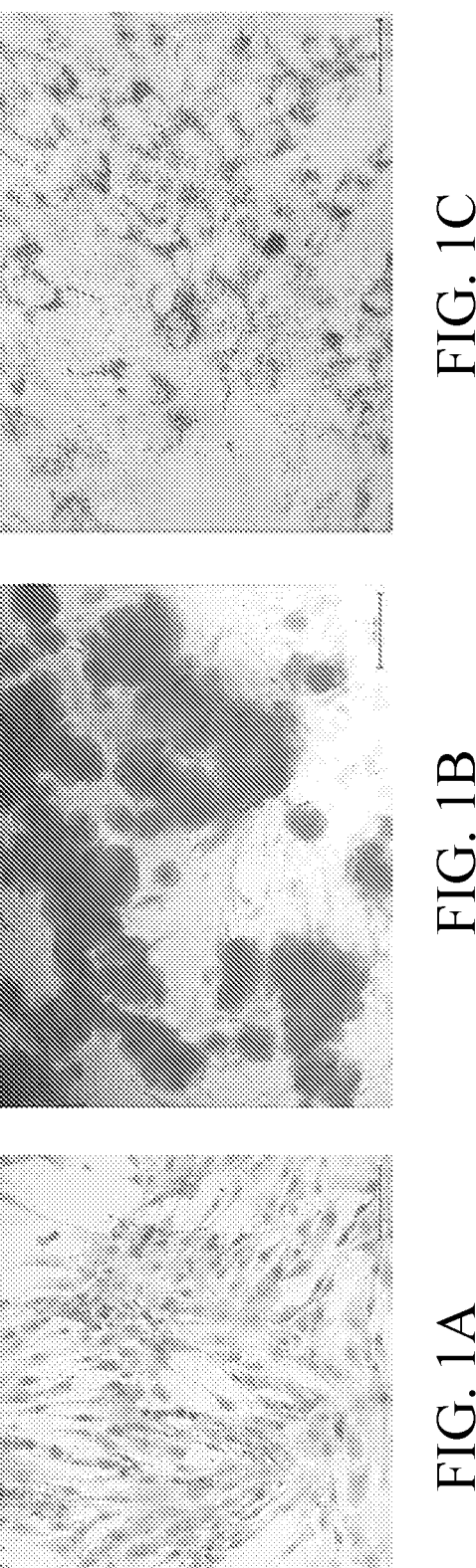
FIGS. 1A-1C are photomicrographs of feline adipose-derived multipotent stromal (stem) cells (ASCs) following culture in stromal medium.

Diabetes mellitus is among the most common feline endocrinopathies, there is no known cure, and the prevalence is steadily increasing. Unregulated glucose levels contribute to serious, permanent health problems in cats of all breeds and ages. Exogenous insulin administration is necessary to maintain healthy glucose levels when pancreatic β cells cease to function. Therapy is often a complex, time consuming process that relies on non-feline insulin formulations. Treatment with xenogeneic insulin is fraught with complications and is time consuming. As many as 30% of cats succumb to consequences of the disease within 1 year of diagnosis.

As described herein, starting feline cells such as adipose-derived multipotent stromal (stem) cells (ASCs) can be transdifferentiated into pancreatic islet cells that secrete insulin in response to glucose. The cells can be used to create implantable tissue grafts to restore β cell function that can be applied in a permanent or removable configuration. The methods and compositions can be used to generate exogenous feline insulin for direct administration to cats.

The pancreatic islet cells produced using the methods and compositions described herein can restore natural insulin production after minimally invasive implantation of custom tissue grafts generated from individual stem cells. Such custom insulin producing grafts (e.g., made from ASCs) that are conducive to minimally invasive implantation may cure diabetes in cats.

As illustrated herein, feline ASCs isolated from subcutaneous adipose tissue or from reproductive organs have endodermal transdifferentiation capability. However, feline ASCs from male donors often have distinct morphology compared to female donors. Induced cells appear to form functional clusters based on zinc accumulation secretion of insulin in response to glucose stimulation, the presence of intracellular insulin, and the pancreatic β-cell specific gene expression. The methods and compositions described herein significantly advance the potential to produce custom feline insulin for exogenous administrations as well as a cell-based therapy for temporary or long term restoration of feline pancreatic β cell function.

The compositions and methods have been customized for feline cells and have been designed to replicate in vivo pancreatic formation and development in cats. In view of species differences, culture methods are most effective when designed for the target species (Buang et al., Arch. Med. Res. 43: 83-88 (2012); Dubey et al., Repro. Fertil. Devel. 26: 213 (2014); Dang et al., Biomed. Res. Ther. 2: 184-192 (2015); Chandra et al., Stem Cells 27: 1941-1953 (2009)).

In the developed a three-stage induction system, N-2 and B-27 can enhance proliferation and protect against reactive oxygen species in the absence of FBS. FBS can provide growth factors, nutrients and hormones for cell proliferation and adhesion. Additionally, there are several extrinsic factors used in the system that have beneficial effects on differentiation of MSCs into insulin producing cells.

Stage I

Stage 1 can involve culturing adult adipose-derived multipotent stromal (stem) cells (ASCs) for about 1-4 days in a first culture medium comprising activin A, sodium butyrate, and 2-mercapethanol.

At Stage 1, activin A and sodium butyrate can direct starting cells such as ASCs to undergo endoderm differentiation. Insulin-transferrin-selenium (ITS), 2-mercaptoethanol, and the supplements can protect starting cells such as ASCs and can reduce the risk of apoptosis. Ultra-low attachment culture plates or culture vessels can be used to enhance formation of three-dimensional cell aggregates. For example, protein coated culture plates or culture vessels can be used. Examples of proteins that can coat the culture plates or culture vessels include collagen, fibronectin, laminin, polylysine, poly-ornithine, or a combination thereof.

Activin A is available commercially from various suppliers, for example, from Invitrogen, PeproTech, StemRD, R&D Systems, and other vendors.

In some cases, agents that have activity like activin A can be used instead of activin A. Activin A is a member of the TGFβ family first identified in late 1980s as an inducer of follicle-stimulating hormone. Activin A is highly conserved in evolution and throughout the animal kingdom. It regulates a variety of biologic processes including cell proliferation, hematopoiesis, wound healing, and fibrosis. Activin A signals through the activin type I (Alk2, 4, or 7) and type II (ActRII or ActRIIB) receptors and shares with TGFβ the activation of the Smad cascade. See, Phillips et al., *Cytokine Growth Factor Rev.* 20(2): 153-64 (2009); Werner, *Cytokine Growth Factor Rev.* 17(3): 157-71 (2006). Examples of TGF-β family members that can be used instead of activin A include the decapentaplegic-Vg-related (DVR) related subfamily of proteins (including bone morphogenetic proteins and the growth differentiation factors), and the TGF-β subfamily.

Activin A and/or other TGFβ family members can be used at a variety of concentrations, for example, at about 0.1 nanomolar to about 20 nanomolar, or from about 0.5 nanomolar to about 15 nanomolar, or from about 1 nanomolar to about 10 nanomolar, or from about 2 nanomolar to about 8 nanomolar, or about 4 nanomolar.

Agents with activities like sodium butyrate can also be used instead of sodium butyrate (or in combination with sodium butyrate). Sodium butyrate is an inhibitor histone deacetylases (HDACs), which are a class of enzymes that remove acetyl groups from an ε-N-acetyl lysine amino acid on a histone. Examples of HDAC inhibitors that can be used include, for example, butyrate, small molecular weight carboxylates (e.g., less than about 250 amu), hydroxamic acids, benzamides, epoxyketones, cyclic peptides, and hybrid molecules. (See, for example, Drummond et al., *Annu Rev Pharmacol Toxicol* 45: 495-528 (2005), (including specific examples therein) which is hereby incorporated by reference in its entirety). Other examples of negative regulators of type 1/II HDACs include: sodium butyrate, phenyl butyrate, or butyrate, suberoylanilide hydroxamic Acid (SAHA; also called Vorinostat and MK0683), valproic acid (and other short chain fatty acids), suramin (e.g., suramin sodium), and combinations thereof.

The HDAC inhibitor can be employed in the compositions and methods described herein in a variety of amounts and/or concentrations. For example, the HDAC inhibitor can be employed at a concentration of about 1 micromolar to about 20 millimolar, or about 10 micromolar to about 15 millimolar, or about 50 micromolar to about 10 millimolar, or about 100 micromolar to about 10 millimolar, or about 0.5 millimolar to about 2 millimolar, or about 1 millimolar in a culture medium solution.

The stage 1 culture medium can include beta-mercaptoethanol at a variety of concentrations. For example, beta-mercaptoethanol can be employed at a concentration of from about 1 micromolar to about 200 micromolar, or from about 5 micromolar to about 100 micromolar, or from about 10 micromolar to about 80 micromolar, or at about 50 micromolar in a culture medium solution.

The stage 1 compositions and methods can include use of other agents including insulin-transferrin-selenium (ITS), supplements, proteins and/or growth factors.

Insulin-transferrin-selenium can be present in various amounts. Insulin-Transferrin-Selenium is available from various commercial venders. Insulin is typically present in culture media at a concentration of about 1 μg/ml to about 100 μg/ml, or from about 3 μg/ml to about 50 μg/ml, or from about 5 μg/ml to about 20 μg/ml, or at about 10 μg/ml. Transferrin is typically present in culture media at a concentration of about 5 μg/ml to about 150 μg/ml, or from about 20 μg/ml to about 100 μg/ml, or from about 30 μg/ml to about 750 μg/ml, or at about 55 μg/ml. Selenium is typically present in culture media at a concentration of about 1 μg/ml to about 100 μg/ml, or from about 3 μg/ml to about 50 μg/ml, or from about 5 μg/ml to about 20 μg/ml, or at about 10 μg/ml. Selenium can be used at a variety of concentrations, for example, at about 5 ng/ml to about 200 ng/ml, or from about 20 ng/ml to about 150 ng/ml, or from about 40 ng/ml to about 100 ng/ml, or from about 50 ng/ml to about 80 ng/ml, or at about 67 ng/ml. In some cases, a commercial preparation of insulin-transferrin-selenium can be employed, for example, from Gibco BRL (Gaithersburg, MD), which is often supplied in concentrated form. For example, 100-fold concentrated insulin-transferrin-selenium preparations can be diluted 1:100 into culture medium.

Examples of proteins that can be included in the stage 1 compositions and methods include serum albumin, collagen, fibronectin, laminin, polylysine, poly-ornithine, or a combination thereof. Examples of growth factors that can be included in the stage 1 compositions and methods include hepatocyte growth factor (HGF) and/or fibroblast growth factor (bFGF).

In some cases, the stage 1 compositions and methods can include supplements such as N-2 supplement, B-27 supplement, or a combination thereof.

Proteins can be included in the stage 1 compositions at a variety of concentrations. For example, proteins (e.g., laminin, collagen, or a combination thereof) can be employed at a concentration of from about 0.1 μg/ml to about 100 μg/ml, or from about 1 μg/ml to about 10 μg/ml, or from about 2 μg/ml to about 7 μg/ml, or at about 5 μg/ml in a culture medium solution. Serum albumin (e.g., BSA) can be employed at a concentration of from about 0.05% to about 10%, or from about 0.1% to about 5%, or from about 0.5% to about 2%, or at about 1% in a culture medium solution.

Growth factors can be included in the stage 1 compositions are a variety of concentrations. For example, growth factors (e.g., HGF, bFGF, or a combination thereof) can be employed at a concentration of from about 0.1 ng/ml to about 200 ng/ml, or from about 1 ng/ml to about 150 ng/ml, or from about 10 ng/ml to about 70 ng/ml, or at about 20 ng/ml to about 50 ng/ml in a culture medium solution.

For example, the stage 1 media can include 4 nM avidin A, 1 mM sodium butyrate, 50 μM 2-mercapethanol, 1% N-2 supplement, 1% B-27 supplement, 5 μg/ml laminin (Corning), 50 ng/ml recombinant human hepatocyte growth factor (HGF), and 20 ng/ml basic fibroblast growth factor (bFGF).

Stage 2

Stage 2 can induce the endoderm cell clusters formed at Stage 1 to provide cells of the pancreatic endodermal lineage. Cells at this stage can be cultured on protein coated culture plates or in protein coated culture vessels.

Stage 2 can involve culturing the first population of cells for 4 to 8 days in a second culture medium comprising insulin-transferrin-selenium, and taurine.

The insulin-transferrin-selenium can be present in various amounts. Insulin-Transferrin-Selenium is available from various commercial venders. Insulin is typically present in culture media at a concentration of about 1 μg/ml to about 100 μg/ml, or from about 3 μg/ml to about 50 μg/ml, or from about 5 μg/ml to about 20 μg/ml, or at about 10 μg/ml. Transferrin is typically present in culture media at a concentration of about 5 μg/ml to about 150 μg/ml, or from about 20 μg/ml to about 100 μg/ml, or from about 30 μg/ml to about 750 μg/ml, or at about 55 μg/ml. Selenium is typically present in culture media at a concentration of about 1 μg/ml to about 100 μg/ml, or from about 3 μg/ml to about 50 μg/ml, or from about 5 μg/ml to about 20 μg/ml, or at about 10 μg/ml. Selenium can be used at a variety of concentrations, for example, at about 5 ng/ml to about 200 ng/ml, or from about 20 ng/ml to about 150 ng/ml, or from about 40 ng/ml to about 100 ng/ml, or from about 50 ng/ml to about 80 ng/ml, or at about 67 ng/ml. In some cases, a commercial preparation of insulin-transferrin-selenium can be employed, for example, from Gibco BRL (Gaithersburg, MD). In some cases, a commercial preparation of insulin-transferrin-selenium can be employed, for example, from Gibco BRL (Gaithersburg, MD), which is often supplied in concentrated form. For example, 100-fold concentrated insulin-transferrin-selenium preparations can be diluted 1:100 into culture medium.

Taurine, or 2-aminoethanesulfonic acid, is an organic compound that is widely distributed in animal tissues. It is a major constituent of bile and can be found in the large intestine.

Taurine introduced into the induction medium can facilitate development of functional β cells. During the induction process, the induced cell clusters can have a morphology similar to the induced 0-cell cluster morphology from other species (see, e.g., Okura et al., J. Artificial Organs 12:123-130 (2009)) and may lose the capacity to attach to the plastic culture. Loss of the ability to attach to plastic is one criterion for identifying mesenchymal stromal cells (MSCs) (Dominici et al., Cytotherapy 8 (2006)). Cells cultured in stromal medium retained their plastic affinity after culture on normal culture plates while those in induction medium did not, further confirming differentiation and maturation.

Taurine can be employed in the compositions and methods described herein in a variety of amounts and/or concentrations. For example, taurine can be employed at a concentration of about 0.01 mM to about 10 mM, or from about 0.03 mM to about 5 mM, or from about 0.05 mM to about 1 mM, or from about 0.1 mM to about 0.7 mM, or from about 0.2 mM to about 0.5 mM, or at about 0.3 mM.

The compositions and methods can include use of other agents including one or more types of sugar, one or more types of protein, one or more types of growth factors, one or more types of supplements, and combinations thereof.

Sugars such as glucose or sucrose can be included in the stage 2 compositions and methods. Sugars can be employed in the compositions and methods described herein in a variety of amounts and/or concentrations. For example, sugars (e.g., glucose) can be employed at a concentration of about 0.1 mM to about 100 mM, or from about 1 mM to about 50 mM, or from about 5 mM to about 30 mM, or from about 10 mM to about 25 mM, or from about 15 mM to about 20 mM, or at about 17.5 mM.

Proteins can be included in the stage 1 compositions at a variety of concentrations. For example, proteins (e.g., laminin, collagen, or a combination thereof) can be employed at a concentration of from about 0.1 μg/ml to about 100 μg/ml, or from about 1 μg/ml to about 10 μg/ml, or from about 2 μg/ml to about 7 μg/ml, or at about 5 μg/ml in a culture medium solution. Serum albumin (e.g., BSA) can be employed at a concentration of from about 0.05% to about 10%, or from about 0.1% to about 5%, or from about 0.5% to about 2%, or at about 1% in a culture medium solution.

Growth factors can be included in the stage 1 compositions are a variety of concentrations. For example, growth factors (e.g., HGF, bFGF, or a combination thereof) can be employed at a concentration of from about 0.1 ng/ml to about 200 ng/ml, or from about 1 ng/ml to about 150 ng/ml, or from about 10 ng/ml to about 70 ng/ml, or at about 20 ng/ml to about 50 ng/ml in a culture medium solution.

In some cases, the stage 1 compositions and methods can include supplements such as N-2 supplement, B-27 supplement, or a combination thereof.

For example, the stage 2 media can include serum free medium (SFM 2) (6 days): DMEM, 17.5 mM glucose, 1% BSA, 1×ITS, 0.3 mM taurine (ACROS Organics, Morris Plains, NJ), 5 μg/ml laminin, 20 ng/ml bFGF, 1% N-2 supplement, 1% B-27 supplement, 50 ng/ml HGF;
Stage 3

Stage 3 can involve culturing the second population of cells for 2 to 6 days in a third culture medium comprising insulin-transferrin-selenium, taurine, glucagon-like peptide 1 (GLP-1), nicotinamide, pentagastrin, and betacellulin.

The insulin-transferrin-selenium can be used at somewhat higher concentrations than employed for stages 1 and 2. For example, insulin is typically present in culture media at a concentration of about 1.5 μg/ml to about 150 μg/ml, or from about 3 μg/ml to about 50 μg/ml, or from about 7 μg/ml to about 30 μg/ml, or at about 15 μg/ml. Transferrin is typically present in culture media at a concentration of about 7.5 μg/ml to about 200 μg/ml, or from about 25 μg/ml to about 150 μg/ml, or from about 50 μg/ml to about 100 μg/ml, or at about 75-80 μg/ml. Selenium can be used at a variety of concentrations, for example, at about 10 ng/ml to about 400 ng/ml, or from about 20 ng/ml to about 300 ng/ml, or from about 40 ng/ml to about 200 ng/ml, or from about 50 ng/ml to about 150 ng/ml, or at about 100 ng/ml. In some cases, a commercial preparation of insulin-transferrin-selenium can be employed, for example, from Gibco BRL (Gaithersburg, MD). In some cases, a commercial preparation of insulin-transferrin-selenium can be employed, for example, from Gibco BRL (Gaithersburg, MD), which is often supplied in concentrated form. For example, 100-fold concentrated insulin-transferrin-selenium preparations can be diluted 1.5:100 into culture medium.

Taurine can be used in amounts that are somewhat greater than the amounts used for Stage 2. For example, taurine can be used in amounts that are about two-fold, or five-fold, or ten-fold, or bout fifteen-fold greater than the amounts used for Stage 2. Taurine can be employed in the stage 3 compositions and methods at a concentration of about 0.005 mM to about 20 mM, or from about 0.01 mM to about 15 mM, or from about 0.05 mM to about 10 mM, or from about 0.1 mM to about 5 mM, or from about 0.2 mM to about 1 mM, or at about 3 mM.

The glucagon-like peptide 1 (GLP-1) can be employed in the compositions and methods described herein in a variety of amounts and/or concentrations. For example, the GLP-1 can be employed at a concentration of about 1 nanomolar to about 300 nanomolar, or about 10 nanomolar to about 200 nanomolar, or about 30 nanomolar to about 150 nanomolar, or about 50 nanomolar to about 120 nanomolar, or at about 100 nanomolar in a culture medium solution.

Nicotinamide is a polyADP-ribose synthetase inhibitor. Other types of polyADP-ribose synthetase inhibitors can be used instead of or in combination with nicotinamide. Examples of polyADP-ribose synthetase inhibitors therefore include nicotinamide, 3-aminobenzamide, 1,5-isoquinolinediol and combinations thereof. The polyADP-ribose synthetase inhibitors (e.g., nicotinamide) can be employed at a concentration of about 0.05 millimolar to about 100 millimolar, or about 0.1 millimolar to about 20 millimolar, or about 0.3 millimolar to about 10 millimolar, or about 0.5 millimolar to about 5 millimolar, or about 1 millimolar in a culture medium solution.

Pentagastrin is a synthetic polypeptide that has effects like gastrin. When administered, it can stimulate the secretion of gastric acid, pepsin, and intrinsic factor. Pentagastrin can be employed in the compositions and methods described herein in a variety of amounts and/or concentrations. For example, pentagastrin can be employed at a concentration of from about 0.1 nanomolar to about 30 nanomolar, or about 1 nanomolar to about 20 nanomolar, or about 3 nanomolar to about 15 nanomolar, or about 5 nanomolar to about 12 nanomolar, or at about 10 nanomolar in a culture medium solution.

Betacellulin is a member of the EGF family of growth factors. It is synthesized primarily as a transmembrane precursor, which is then processed to mature molecule by proteolytic events. It can be a ligand for EGF receptor Betacellulin can be employed in the compositions and methods described herein in a variety of amounts and/or concentrations. For example, betacellulin can be employed at a concentration of from about 0.1 ng/ml to about 200 ng/ml, or from about 1 ng/ml to about 100 ng/ml, or from about 3 ng/ml to about 50 ng/ml, or from about 5 ng/ml to about 25 ng/ml, or at about 100 ng/ml, in a culture medium solution.

The stage 3 compositions and methods can include use of other agents such as sugars, proteins, supplements, and amino acids.

Sugars such as glucose or sucrose can be included in the stage 2 compositions and methods. Sugars can be employed in the compositions and methods described herein in a variety of amounts and/or concentrations. For example, sugars (e.g., glucose) can be employed at a concentration of about 0.1 mM to about 100 mM, or from about 1 mM to about 50 mM, or from about 5 mM to about 30 mM, or from about 10 mM to about 25 mM, or from about 15 mM to about 20 mM, or at about 17.5 mM.

Proteins can be included in the stage 1 compositions at a variety of concentrations. For example, proteins (e.g., laminin, collagen, or a combination thereof) can be employed at a concentration of from about 0.1 μg/ml to about 100 μg/ml, or from about 1 μg/ml to about 10 μg/ml, or from about 2 μg/ml to about 7 μg/ml, or at about 5 μg/ml in a culture medium solution. Serum albumin (e.g., BSA) can be employed at a concentration of from about 0.05% to about 10%, or from about 0.1% to about 5%, or from about 1% to about 3%, or at about 1.5% in a culture medium solution.

Growth factors can be included in the stage 1 compositions are a variety of concentrations. For example, growth factors (e.g., HGF, bFGF, or a combination thereof) can be employed at a concentration of from about 0.1 ng/ml to about 200 ng/ml, or from about 1 ng/ml to about 150 ng/ml, or from about 10 ng/ml to about 70 ng/ml, or at about 20 ng/ml to about 50 ng/ml in a culture medium solution.

In some cases, the stage 1 compositions and methods can include supplements such as N-2 supplement, B-27 supplement, or a combination thereof.

In some cases, the third stage compositions and methods can include use of the following serum free media (SFM 3) for 4 days: DMEM, 17.5 mM glucose, 1.5% BSA, 1.5×ITS, 3 mM taurine, 100 nM glucagon-like peptide 1 (GLP-1), 1 mM nicotinamide, 1× non-essential amino acids (NEAA, e.g., from Gibco), 10 nM pentagastrin, 1% N-2 supplement, 1% B-27 supplement, 50 ng/ml HGF, 20 ng/ml bFGF, 5 μg/ml laminin, 10 ng/ml betacellulin.

At a third stage, the cell clusters are converted into functional pancreatic hormone-expressing islet-like cell aggregates with the help of glucagon-like peptide 1 (GLP-1), nicotinamide, taurine, and β-cellulin. Nicotinamide can promote the maturation of precursor cells into insulin-producing cells and increase the rate of proinsulin biosynthesis. Addition of β-cellulin and nicotinamide to the Stage 3 induction medium can promote β cell maturation and can generate cells that express endocrine hormones including insulin and glucagon. Theophylline can also be used in the Stage 3 induction medium.

As illustrated herein, the induced cell clusters produced during stage 3 were specifically labeled with the zinc-chelating dye dithizone (DTZ), which stains β-cells due to the presence of zinc in insulin-containing secretory granules (D'Amour et al., Nature Biotech. 24: 1392 (2006)). Immunofluorescence, DTZ staining, and immune electron microscopy results confirmed that the induced cells produced using the compositions and methods described herein expressed insulin. As shown herein, RT-PCR showed that the induced cells coexpressed insulin, glucagon, and somatostatin. These results are in accordance with normal pancreatic development, in which immature islets are known to coexpress pancreatic hormones (Chandra et al. Stem Cells 27: 1941-1953 (2009)).

Male/Female

Surprisingly, the mRNA levels of Pax6 and Glut2 were different in male and female ASCs at such an early induction stage, indicating that the cells from male cats may have higher sensitivity than that from female cats. For example, human male ASCs may have greater osteogenic potential than female ASCs. Pax6 is a transcription factor that can transactivate the insulin promoters (Sander et al., *Genes & development* 11:1662-1673 (1997)). The higher expression of Pax6 in male ASCs at early induction stages may indicate that the male ASCs undergo pancreatic β cell differentiation more easily than female.

The results described herein show that male and female ASCs have endodermal transdifferentiation capability. The induced cell clusters can secrete insulin with the glucose stimulation. In the clinical context, these results demonstrate the potential for stem cell-based therapy to treat feline diabetes. The mechanisms of the transdifferentiation in feline ASCs are not clear. Hence, it may not be possible to predict what compositions and methods would successfully transdifferentiate feline starting cells into cells that can secrete insulin cells. However, the methods and compositions described herein do transdifferentiate feline ASCs into functional insulin-producing cells, demonstrating that such methods and compositions are provide a viable therapeutic option for feline diabetes.

Kits

Also provided are kits for generating pancreatic precursor cells and/or pancreatic cells. The kits can contain any of the compositions described herein and instructions for using the compositions for generating definitive endoderm cells and/or pancreatic precursor cells and/or pancreatic cells. Each of the compositions can be separately packaged. Each composition can contain any of the compounds or proteins described herein at a concentration that is convenient for addition to a culture of cells. For example, compositions can be concentrated to about 10×, 50×, 100×, or 1000× of the concentration at which it would be employed to pancreatic precursor cells and/or cells that can secrete insulin cells and/or pancreatic beta cells. The instructions can provide guidance for appropriate addition (dilution) of the compositions into a cell culture, and/or guidance on other culture conditions (e.g., appropriate cell culture media, an appropriate duration of exposure to the compositions, etc.). The instructions can also provide guidance on the selection of starting cells for generating pancreatic precursor cells and/or cells that can secrete insulin cells and/or pancreatic cells. In addition, the instructions can provide information for testing and/or recognition of the generated pancreatic precursor cells and/or cells that can secrete insulin cells and/or pancreatic cells.

The kits can also provide components and instructions for administering pancreatic precursor cells and/or cells that can secrete insulin cells and/or pancreatic beta cells to mammalian (e.g., feline) subjects. The instructions can provide guidance on the numbers and the type(s) (phenotype) of cells to be administered. The instructions can also provide instructions for administration of pancreatic precursor cells and/or cells that can secrete insulin cells and/or pancreatic beta cells by surgical implantation or by infusion. For example, the kits can provide diluents, pharmaceutically acceptable carriers, scalpels, syringes, catheters, bandages, antiseptics, and the like to permit administration of cells.

Mixtures

The pancreatic precursor cells and/or cells that can secrete insulin cells and/or pancreatic cells can be present in any of the foregoing compositions. The pancreatic precursor cells and/or cells that can secrete insulin cells and/or pancreatic cells can also be present in a therapeutically acceptable carrier such as saline, phosphate buffered saline, or other aqueous carrier. Such a combination of the compositions described herein, or a therapeutically acceptable carrier, with pancreatic precursor cells and/or cells that can secrete insulin cells and/or pancreatic cells can be referred to as a mixture.

The mixtures can contain about 1 to about $10^{10}$ pancreatic precursor cells and/or cells that can secrete insulin cells and/or pancreatic (e.g., beta) cells.

The pancreatic precursor cells and/or cells that can secrete insulin cells and/or pancreatic cells generated as described herein can be isolated, separated, or purified from culture media, compositions, or other mixtures in which they are generated. The pancreatic precursor cells and/or cells that can secrete insulin cells and/or pancreatic cells generated as described herein can be enriched or cultured to increase the proportion or numbers of desired cells in the population. Any such isolate, separation, purification, enrichment, or culture is a mixture as described herein.

An isolating step can include providing the cells in the cell culture with a reagent which binds to a marker expressed in the desired cell type (e.g., pancreatic precursor cells, and/or cells that can secrete insulin cells and/or pancreatic cells) but which is not substantially expressed in other cells present in the cell culture. The reagent-bound cells can be separated from the non-reagent-bound cells by numerous methods. For example, an antibody against a marker that is selectively present on the desired cells can be provided to cells in a cell culture. Antibody-bound cells can then be separated from other cells in the culture by, for example, fluorescent activated cell sorting (FACS), binding the antibody to a solid support or isolating appropriately tagged antibody in a magnetic field. In some embodiments, the antibody is released from the cells after the separation process.

As an alternative means of separation, at least some of the desired cells can be separated from at least some of the other cells in the culture by specifically fluorescently labeling the desired cells in culture and then separating the labeled cells from the unlabeled cells by FACS.

An enriched cell population of pancreatic progenitor cells, and/or cells that can secrete insulin cells, and/or pancreatic beta cells produced, for example, by an isolating step can be substantially free of cells other than pancreatic progenitor cells, and/or cells that can secrete insulin cells and/or pancreatic beta cells. In other embodiments, the enriched cell populations can have at least about 50% to at least about 100% pancreatic progenitor cells, and/or cells that can secrete insulin cells and/or pancreatic beta cells. In still other embodiments, the enriched cell populations comprise from at least about 75%, at least about 80%, at least about 85%, at least about 90%, at least about 95%, at least about 96%, at least about 97%, at least about 99%, or at least about 100% pancreatic progenitor cells, and/or cells that can secrete insulin cells, and/or pancreatic beta cells.

In some instances, the pancreatic progenitor cells, cells that can secrete insulin cells, and/or pancreatic beta cells are expanded, for example, by culturing the cells under conditions that permit cell division. For example, some embodiments include a culturing step that comprises plating a cell population on a surface such as a culture plate. In some embodiments, the cells are plated on a surface coated with a protein, poly-amino acid or carbohydrate (e.g., collagen, fibronectin, laminin, polylysine, poly-ornithine, or a combination thereof).

In other embodiments, the culturing step comprises incubating the cell population or portion thereof in an expansion medium comprising about 2% (v/v) serum. In some embodiments, the serum concentration can range from about 0% (v/v) to about 20% (v/v). For example, in some methods described herein, the serum concentration of the medium can be about 0.05% (v/v), about 0.1% (v/v), about 0.2% (v/v), about 0.3% (v/v), about 0.4% (v/v), about 0.5% (v/v), about 0.6% (v/v), about 0.7% (v/v), about 0.8% (v/v), about 0.9% (v/v), about 1% (v/v), about 2% (v/v), about 3% (v/v), about 4% (v/v), about 5% (v/v), about 6% (v/v), about 7% (v/v), about 8% (v/v), about 9% (v/v), about 10% (v/v), about 15% (v/v) or about 20% (v/v). In some embodiments, serum replacement is included in the medium, and no serum is employed.

Using the methods described herein, cell populations or cell cultures can be enriched in pancreatic progenitor (precursor) cells, cells that secrete insulin, and/or pancreatic beta cell content by at least about 2-fold to about 1000-fold as compared to cell populations or cell cultures produced by the methods and compositions described herein. In some embodiments, pancreatic progenitor (precursor) cells, cells that secrete insulin, and/or pancreatic beta cells can be enriched by at least about 5-fold to about 500-fold as compared to cell populations or cell cultures produced by the methods and compositions described herein. In other embodiments, pancreatic progenitor, cells that secrete insulin, and/or pancreatic beta cells can be enriched from at least about 10- to about 200-fold as compared to cell populations or cell cultures produced by the methods and compositions described herein. In still other embodiments, pancreatic progenitor, cells that secrete insulin, and/or pancreatic beta cells can be enriched from at least about 20- to about 100-fold as compared to cell populations or cell cultures produced by the methods and compositions described herein. In yet other embodiments, pancreatic progenitor, cells that secrete insulin, and/or pancreatic beta cells can be enriched from at least about 40- to about 80-fold as compared to cell populations or cell cultures produced by the methods and compositions described herein. In certain embodiments, pancreatic progenitor, cells that secrete insulin, and/or pancreatic beta cells can be enriched from at least about 2- to about 20-fold as compared to cell populations or cell cultures produced by the methods and compositions described herein.

Some embodiments described herein relate to cell cultures or cell populations comprising from at least about 5% pancreatic progenitor, cells that secrete insulin, and/or pancreatic beta cells to at least about 95% pancreatic progenitor, cells that secrete insulin, and/or pancreatic beta cells. In some embodiments the cell cultures or cell populations comprise mammalian cells. In preferred embodiments, the cell cultures or cell populations comprise feline cells. For example, certain specific embodiments relate to cell cultures comprising feline cells, wherein from at least about 5% to at least about 95% of the cells are pancreatic progenitor, cells that secrete insulin, and/or pancreatic beta cells. Other embodiments relate to cell cultures comprising feline cells, wherein at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or greater than 90% of the cells are pancreatic progenitor, cells that secrete insulin, and/or pancreatic beta cells. In embodiments where the cell cultures or cell populations comprise mammalian feeder cells, the above percentages are calculated without respect to the feeder cells in the cell cultures or cell populations.

Therapy

Also described herein is a method for treating a subject (e.g., a feline subject) suffering from, or at risk of developing, diabetes. This method involves generating pancreatic progenitor, cells that secrete insulin, and/or pancreatic beta cells as described herein, and administering or implanting the cells into a mammalian subject (e.g., a feline subject).

The pancreatic progenitor, cells that secrete insulin, and/or pancreatic beta cells can be implanted as dispersed cells or formed into clusters. Alternatively, pancreatic progenitor, cells that secrete insulin, and/or pancreatic beta cells can be infused into the subject, for example, via a hepatic portal vein. Alternatively, cells may be provided in biocompatible degradable polymeric supports, porous non-degradable devices or encapsulated to protect from host immune response. Cells may be implanted into an appropriate site in a subject. The implantation sites include, for example, the liver, natural pancreas, renal subcapsular space, omentum, peritoneum, subserosal space, intestine, stomach, or a subcutaneous pocket.

The amount of cells used in implantation depends on a number of various factors including the subject's condition and response to the therapy, and can be determined by one skilled in the art. For example, the number of cells administered can range from about 1000 to about $10^9$, or from about 1000 to about $10^8$, or from about 1000 to about $10^7$, or from about 1000 to about $10^6$, or from about 10000 to about $10^7$.

In one aspect, a method is provided for treating a subject suffering from, or at risk of developing diabetes. This method involves culturing a starting cell population, differentiating or redirecting the cultured cells in vitro into a first population of cells that express at least one of the following genes: Nkx 6.1, Pax6, Isl1, or Glut-2; differentiating the first population of cells into a second population containing pancreatic progenitor cells and administering the second population of cells to a subject. In some instances pancreatic progenitor cells are enriched within the second population or purified from the second population of cells to generate a third population of cells that is substantially free of non-pancreatic cells.

The cells to be administered can be incorporated into a three-dimensional support. The cells can be maintained in vitro on this support prior to implantation into the subject. Alternatively, the support containing the cells can be directly implanted in the subject without additional in vitro culturing. The support can optionally be incorporated with at least one pharmaceutical agent that facilitates the survival and function of the transplanted cells.

Support materials suitable for use include tissue templates, conduits, barriers, and reservoirs useful for tissue repair. In particular, synthetic and natural materials in the form of forms, sponges, gels, hydrogels, textiles, and nonwoven structures, which have been used in vitro and in vivo to reconstruct or regenerate biological tissue, as well as to deliver chemotactic agents for inducing tissue growth, are suitable for use in practicing the methods described herein. See, for example, the materials disclosed in U.S. Pat. Nos. 5,770,417, 6,022,743, 5,567,612, 5,759,830, 6,626,950, 6,534,084, 6,306,424, 6,365,149, 6,599,323, 6,656,488, U.S. Published Application 2004/0062753 A1, U.S. Pat. Nos. 4,557,264 and 6,333,029, each of which is specifically incorporated by reference herein in its entirety.

The mammalian subject can be a domestic animal, or a laboratory animal. In some cases, the subject is a feline subject.

Definitions

As used herein and in the appended claims, the singular forms "a," "an," and "the" include plural reference unless the context clearly dictates otherwise. Thus, for example, a reference to "a compound," "a cell," "a nucleic acid" or "a polypeptide" includes a plurality of such compounds, cells, nucleic acids or polypeptides (for example, a solution of cells, nucleic acids or polypeptides, a suspension of cells, or a series of compound, cell, nucleic acid or polypeptide preparations), and so forth.

The following Examples describe some experimental work performed during development of the invention. Appendix A may provide additional information about the invention.

Example 1: Materials and Methods

This Example describes some of the materials and methods employed in the development of the invention.

Feline ASC Isolation

Feline ASCs were isolated during routine sterilization of 8 male and 8 female adult cats. Adipose tissue was isolated with sharp dissection, minced, and digested in type I collagenase (33 ml/g adipose tissue, Worthington Biochemical, Lakewood, NJ) within 4 h of harvest. Tissues from each cat (n=5) were divided into three equal portions, and each portion was digested by one of three methods: 1) 0.1% type I collagenase in DMEM, 0.5 h, 60 rpm (Classic); 2) 0.3% type I collagenase in Kreb's Ringer buffer (KRB), 0.5 h, 1,000 rpm stirring (New); and 3) 0.3% type I collagenase in KRB, 1 h, 1,000 rpm stirring (Hour). Tissue was added to collagenase solution in a 30 ml glass jar and stirred with a stir bar at 37° C. for the New and Hour digestion methods. For the Classic digestion method, digestion mixtures within glass jars were agitated on a three-dimensional plate shaker at 37° C. Digests were filtered and then centrifuged (260 g, 5 min). Resulting SVF pellets were resuspended in 5 ml red cell lysis buffer (0.16 mol/L $NH_4Cl$, 0.01 mol/L $KHCO_3$, 0.01% EDTA) followed by cell seeding in 10 mm cell culture dishes in stromal medium (DMEM-Ham's F12, 10% fetal bovine serum (FBS, Hyclone), 1% antibiotic/antimycotic solution). Medium was refreshed after overnight incubation under standard conditions (37° C., 5% $CO_2$) and then every 2-3 days. The total number of colonies with 20 or more cells was determined after 7 days of culture. MSC density was then calculated as colony number/adipose weight (g). The New method was selected to isolate ASCs for the remainder of the study based on the highest number of colonies/g tissue. When SVF cells reached 80% confluence, they were detached with 0.25% trypsin and 0.1% EDTA. Cells were seeded at a density of $5\times10^3$ cells/cm$^2$ for P0 and all subsequent passages for evaluation of fresh cells. To prepare revitalized cells, aliquots ($5\times10^5$ cells) of P0 cells were frozen in cryopreservation medium (80% FBS, 10% DMEM, 10% dimethyl sulfoxide) in liquid nitrogen for 30 days. Cells were then revitalized and seeded at a density of $5 \times 10^3$ cells/cm$^2$ in stromal medium. Revitalized cells were subsequently cultured and evaluated identically to fresh cells.

Study Design

For the purposes of this study, the stromal vascular fraction was the primary cell isolate, and passage (P) 0 was the first cell passage. Fresh cells were expanded to P3 and then paired samples were cultured in stromal or three-step islet cell induction medium. The zinc concentration, insulin production, and ultrastructure was compared between stromal cells and the induced cells from stage 3. Multipotent capacity and lineage specific gene expression (insulin, NK6 homeobox 1 (NK6.1), proto-oncogene tyrosine-protein kinase ROS1 (ROS1), somatostatin (STS), ISL LIM homeobox 1 (Isl1), glucagon (GCG), paired box 6 (Pax6), AKT serine/threonine kinase 1 (AKT1), Ras-related protein Rab-2A (RAB2A), hexokinase 1 (HK1), and glucose transporter 2 (Glut2)) were compared between culture conditions in male and female donors. All materials and reagents were from Sigma-Aldrich, St. Louis, MO unless otherwise noted.

Cell Isolation

Tissue was minced and digested with 0.3% type I collagenase (Worthington Biochemical Corporation, Lakewood, NJ) in Kreb's Ringer buffer (KRB) for 30 minutes, 1,000 rpm stirring with a stir bar at 37° C. After filtering (100 μm nylon cell strainers, BD Falcon, Bedford, MA) and centrifugation (260×g, 5 min), the resulting SVF pellets were resuspended in 5 ml red blood cell lysis buffer (0.16 mol/L NH4Cl, 0.01 mol/L KHCO3, 0.01% ethylenediaminetetraacetic acid (EDTA)) for 5 min. The SVF was collected after centrifugation (260×g, 5 min) and seeded in 10-mm cell culture dishes in stromal medium (Dulbecco's modified Eagle's medium F-12 (DMEM/F-12, Hyclone, Logan, UT), 1% antibiotic/antimycotic solution (MP Biomedical, Irvine, CA), 10% fetal bovine serum (FBS, Hyclone)). Stromal medium was refreshed after 24 hours and then every 3 days.

After 70-80% confluence, the SVF cells were detached with 0.05% trypsin (Hyclone) and cells were seeded in T75 flasks with the density of 5×103 cells/cm2 for P0 and all subsequent passages. Procedures performed at temperatures other than room temperature are indicated.

Multipotentiality

Cell isolates were tested to confirm multipotentiality, P1 fibroblastic colony formation and adipogenic and osteogenic differentiation. For fibroblastic colony formation, P1 cells were cultured in stromal medium for 7 days, fixed with 4% formalin, and stained with 0.1% toluidine blue. To assess adipogenesis, cells were cultured in stromal medium to 70-80% confluence, washed with phosphate buffered saline (PBS, Hyclone) and then cultured in adipogenic medium (Table 1) for 10 days. They were then fixed with 4% neutral paraformaldehyde (PFA) and stained with oil red O. For osteogenesis, the cells were cultured in stromal medium as above, then in osteogenic preinduction medium for 10 days followed by osteogenic induction medium (Table 1) for another 10 days. Colonies were fixed with 70% ice cold ethanol and stained with 2% alizarin red.

Differentiation of Feline ASCs into IPCs

Cell isolates were culture expanded to P3. At 70-80% confluence, they were seeded in 6-well ultra-low attachment plates (Corning, Corning, NY) at $1 \times 10^6$ cells/well and cultured for 7 days in stromal medium. A three-stage protocol was used to induce 0-cell islet-like clusters (Table 1). The cells in ultra-low attachment plates were incubated in serum free medium (SFM) 1 for 2 days as stage 1 and then in SFM 2 for another 6 days at stage 2. Cells were then manually transferred to a standard 6-well plate (Thermo Fisher Scientific, Waltham, MA, USA) and cultured in stage 3 induction medium for another 4 days in standard 6-well plates. All media were refreshed every 2 days and the medium was refreshed every 24 hours in stage 3. Paired cells were cultured in stromal medium in standard 6-well plates throughout the induction process.

TABLE 1

| Composition of induction medium for differentiation | |
|---|---|
| Medium | Composition |
| Adipogenic medium | Minimum essential medium alpha (α-MEM), 10% rabbit serum, 10% FBS, 10 nM dexamethasone, 5 μg/ml insulin, 50 μM 5,8,11,14-eicosatetraynoic acid (ETYA, Cayman, Ann Arbor, MI), 100 μM indomethacin |
| Osteogenic preinduction medium | DMEM, 10% FBS, 100 nM dexamethasone, 0.25 mM L-ascorbic acid |
| Osteogenic induction medium | Osteogenic preinduction medium supplemented with 10 mM β-glycerophosphate |
| β-cell induction medium | Stage 1: SFM 1 (2 days): DMEM, 17.5 mM glucose, 1% BSA (bovine serum albumin), 1× insulin-transferrin-selenium (ITS, Gibco BRL, Gaithersburg, MD), 4 nM activin A (R&D Systems Inc., Minneapolis), 1 mM sodium butyrate, 50 μM 2-mercapethanol, 1% N-2 supplement (R&D Systems Inc.), 1% B-27 supplement (Gibco), 5 μg/ml laminin (Corning), 50 ng/ml recombinant human hepatocyte growth factor (HGF, EMD Millipore, Temecula, CA), 20 ng/ml basic fibroblast growth factor (bFGF, Gibco); |

TABLE 1-continued

| Composition of induction medium for differentiation | |
| --- | --- |
| Medium | Composition |
| | Stage 2:<br>SFM 2 (6 days): DMEM, 17.5 mM glucose, 1% BSA, 1× ITS,<br>0.3 mM taurine (ACROS Organics, Morris Plains, NJ), 5 µg/ml<br>laminin, 20 ng/ml bFGF, 1% N-2 supplement, 1% B-27<br>supplement, 50 ng/ml HGF;<br>Stage 3<br>SFM 3 (4 days): DMEM, 17.5 mM glucose, 1.5% BSA, 1.5×<br>ITS, 3 mM taurine, 100 nM glucagon-like peptide 1 (GLP-1,<br>TOCRIS bioscience, Ellisville, MO), 1 mM nicotinamide<br>(ACROS Organics), 1× non-essential amino acids (NEAA,<br>Gibco), 10 nM pentagastrin (TOCRIS bioscience), 1% N-2<br>supplement, 1% B-27 supplement, 50 ng/ml HGF, 20 ng/ml bFGF,<br>5 µg/ml laminin, 10 ng/ml betacellulin (R&D Systems) |

Dithizone Staining—Zinc Concentration

Following the induction process, cells were incubated with dithizone (DTZ, Fisher Scientific, Fairlawn, NJ) solution (10 µl DTZ working solution (1 mg/ml in dimethyl sulfoxide (Fisher Scientific)) in 1 ml of the culture medium) for 30 min at 37° C. Cells were washed in PBS after incubation and imaged with light microscope.

Immunohistochemistry—Intra-Cellular Insulin

The Dylight 633 antibody labeling kit (Thermo Fisher Scientific, Somerset, NJ) was used to label the antibody goat anti insulin according to the manufacturer's instruction. Briefly, 100 µl antibody solution (1 mg/ml) was mixed with κ µl supplied borate buffer and the mixture was incubated with Dylight Reagent for 60 min and protected from light. The labeling reaction was mixed with resin and then centrifuged (1000×g, 1 min) to collect the labeled antibody.

Cells were washed with PBS and fixed overnight in 4% neutral PFA. They were permeabilized with 0.5% Triton X-100 in PBS and then incubated with the labeled antibody goat anti insulin (1:200 in PBS, Santa Cruz Technologies, CA) for 30 min. After incubation, the cells were washed with PBS and then cytoskeletal actins was stained with β actin-FITC for 30 min (1:500 in PBS, Neomarkers, Fremont, CA). Photomicrographs were obtained for all labeled cells with confocal laser scanning microscopy (CLSM, Leica TCS SP2, Leica, Wetzlar, Germany).

Glucose Challenge Assay—Glucose Sensitivity

The induced islet-like cell clusters were collected and washed twice with PBS. The islet-like cell clusters were incubated with KRB buffer for 1 hour at 37° C., followed by incubation with KRB buffer supplemented with different glucose concentrations (25 and 55 mM) for 30 min at 37° C. Following incubation, the medium was collected and stored at −80° C. until further use. The stored medium was analyzed for insulin content using a feline specific enzyme-linked immunosorbent assay (ELISA) kit (Mybiosource, San Diego, CA). The cells cultured in stromal medium were used as a control.

Transmission Electron Microscopy—Ultrastructure

Following a PBS rinse, cells were fixed in 2% PFA and 2.5% glutaraldehyde in 0.1 M PBS for 10 min. The samples were centrifuged (350×g, 5 min) and then fixed with fresh fixative with gentle agitation for 2 hours. They were mixed with equal amounts of 3% agarose and the mixture was placed to a glass slide. When the mixture solidified, it was sliced into cubes. The cubes were washed with 0.1 M PBS and 0.08M glycine 5 times (15 min/time) followed by incubation with 2% osmium tetroxide in 0.1 M PBS in the darkness for 1 hour to fix the cells. The samples were washed with $H_2O$ and dehydrated in a series of ethanol-distilled water solutions. The dehydrated samples were infiltrated with 1:1 ethanol and LR white resin for 2 hours, and then infiltrated with 100% LR white resin for another 2 hours. Embedded samples were placed into the bottom of a beem capsule and incubated in an 18° C. oven for 24 hours. Ultra-thin sections (90 nm) were cut and stained with 2% uranyl acetate and lead citrate. Some sections were directly evaluated with transmission electron microscopy (JEOL JEM-1400, Japan). The other sections were blocked in 5% BSA in PBS for 30 min and then incubated with goat anti insulin in 0.1% BSA in PBS (1:20) for another 90 min. After incubation, the sections were washed in 0.1% BSA in PBS 6 times (5 min/time) and then incubated in secondary antibody (rabbit anti goat IgG-Gold, Sigma-Aldrich) in 0.1% BSA in PBS for another 90 min. After incubation, the sections were washed with 0.1% BSA buffer and PBS, respectively. The sections were then fixed in 2% glutaraldehyde in PBS for 5 min and contrasted with 2% uranyl acetate and lead citrate after being thoroughly washed in distilled water. Gold labeled sections were observed with TEM.

Scanning Electron Microscopy—Surface Ultrastructure

Cells were collected by filtration and fixed in 2% PFA and 2% glutaraldehyde in 0.1 M PBS for 15 min. The solution was extracted into a 10 ml syringe with a Swinney filter holder fitted with a 2 µm pore polycarbonate with 13 mm diameter. Entrapped cells on the filtered were fixed as before another 15 min and then rinsed with 0.1 M PBS and distilled water. The filter was removed from the syringe and dried with hexamethyldisilazane (HMDS, Electron Microscopy Sciences, Fort Washington, PA) for 30 min, 1:1 100% ethanol and HDMS, and 2 changes for 30 min each with 100% HDMS. Finally the HDMS was removed and the samples were placed in a hood overnight to air-dry. The dried samples were mounted onto aluminum SEM stubs, coated with platinum in an EMS 550× sputter coater and imaged with JSM-6610 High vacuum mode SEM (JEOL Ltd., Japan).

RT-PCR—Gene Expression

Total RNA was isolated from cells harvested from each induction stage (EZNA® MicroElute Total RNA kit, Omega, Bio-Tek, Norcross, GA). The quality and concentration was determined spectrophotometrically (NanoDrop ND-1000; NanoDrop Technologies, Wilmington, DE), and cDNA synthesized (Maxima First-Strand cDNA synthesis kit, Thermo Scientific, Waltham, MA). Feline pancreatic target gene levels (insulin, Isl1, HK1, Glut-2, NK6.1, ROS1, STS, GCG, Pax6, AKT1, and RAB2A) (Table 2) were quantified with real-time RT-PCR using the Thermo Fisher Absolute™ Blue QPCR Rox Mix technology and an ABI Prism 7900 HT Sequence Detection System (Applied Biosystems, Foster City, CA) using feline-specific primers. The ΔCt values were determined relative to the reference gene β-actin.

TABLE 2

| Primer Sequences | | | |
|---|---|---|---|
| Lineage | Primer | Sequences | Accession No. |
| Housekeeping | β-actin | F: AGCCTTCCTTCCTGGGTATG SEQ ID NO: 1 R: ACAGCACCGTGTTAGCGTAG SEQ ID NO: 2 | XM_006941899.3 |
| Transcription Factor | Nkx 6.1 | F: AACGAAATACTTGGCGG SEQ ID NO: 3 R: CCAGAGGCTTGTTGTAGTCG SEQ ID NO: 4 | XM_019829291.1 |
| Transcription Factor | Pax6 | F: GGCAATCGGTGGTAGTAA SEQ ID NO: 5 R: CTTGGTATGTTATCGTTGG SEQ ID NO: 6 | XM_019812231.1 |
| Transcription Factor | Isl1 | F: CAAGGACAAGAAGCGGAG SEQ ID NO: 7 R: CTGGGTTTGCCTGTAAGC SEQ ID NO: 8 | XM_003981424.3 |
| Transcription Factor | Glut 2 | F: TTGGCTTGGATGAGTTACG SEQ ID NO: 9 R: GACTTTCCTTTGGTTTCCG SEQ ID NO: 10 | XM_003991916.3 |
| Protein | Insulin | F: CTTCGTCAACCAGCACC SEQ ID NO: 11 R: ACAGCATTGCTCCACGA SEQ ID NO: 12 | XM_019811180.1 |
|  | Glucagon | F: TGAACACCAAGAGGAACAA SEQ ID NO: 13 R: ACCAGCCAAGCAATGAAT SEQ ID NO: 14 | XM_006935320.2 |
|  | Somato-statin | F: CCAGACAGAGAACGATGCC SEQ ID NO: 15 R: CAGGGTTTGAGTTAGTGGA SEQ ID NO: 16 | XM_003991805.4 |
| Oncogene | ROS1 | F: AACAACAGCCTCTACTACAG SEQ ID NO: 17 R: TATCCTCCGACCGAATCC SEQ ID NO: 18 | XM_019831130.1 P |
|  | Akt1 | F: CCAACACCTTCATCATCCG SEQ ID NO: 19 R: CCATCATTTCCTCCTCCTG SEQ ID NO: 20 | NM_001322435.1 |
|  | RAB2A | F: ACAGACAAGAGGTTTCAGC SEQ ID NO: 21 R: TATGACCGTGTGATGGAAC SEQ ID NO: 22 | XM_019822712.1 |
|  | HK1 | F: TGAGAAGATGGTGAGTGGC SEQ ID NO: 23 R: GGCAGAGCGAAATGAGAC SEQ ID NO: 24 | XM_006937834.3 |

US 12,584,110 B2

23

Statistical Analysis

All results are presented as least squares (LS) mean±SEM. Statistical analyses were performed with the JMP statistical package (v 13.0.0, SAS Institute Cary, NC). Mixed ANOVA models were used to evaluate insulin levels between glucose concentrations within genders and between genders within glucose concentrations. The same models were used to evaluate target gene expression among induction stages within genders and between genders within induction stages. Tukey's post hoc tests were applied for multiple group comparisons ($p<0.05$).

Example 2: ASC Multipotentiality

All ASC isolates following culture in stromal medium displayed osteogenic and adipogenic differentiation based on histochemical staining. Cells had a fibroblastic shape when cultured in stromal medium (FIG. 1A). Colony calcium stained with alizarin red following culture in osteogenic medium (FIG. 1B), and lipid droplets stained with oil red O after adipogenic medium culture (FIG. 1C).

Example 3: Cell Morphology

Figure 2C:
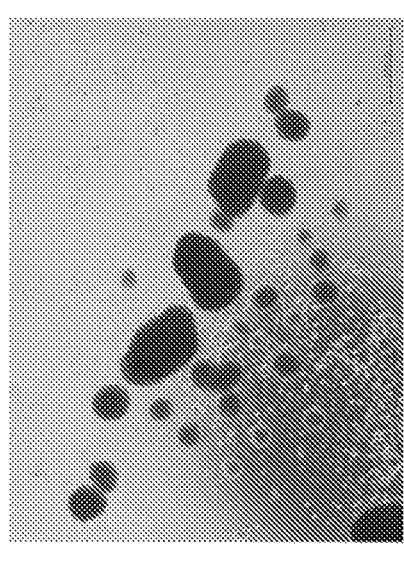
FIG. 2A-2C are light photomicrographs of fresh feline P3 ASCs.
Figure 2B:
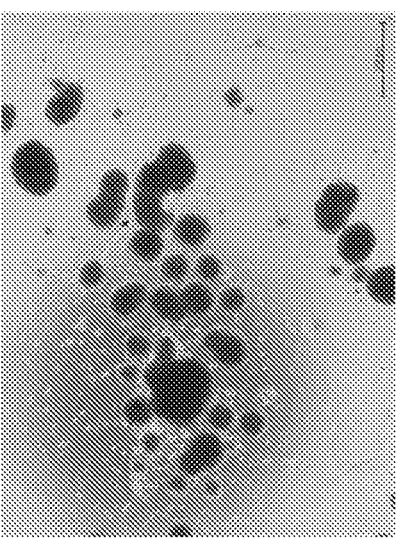
Figure 2A:
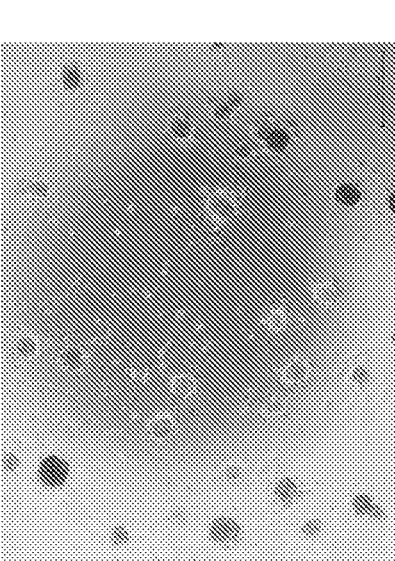

All ACSs cultured in ultralow attachment plates formed cell clusters. Following transfer to a standard six well culture plates, cells cultured in stromal medium attached to the plate in colony formation within 24 hours (FIG. 2A). The vast majority of those cultured in induction medium did not attach at any point and remained as detached cell clusters (FIGS. 2B and 2C).

Example 4: Dithizone Staining—Zinc Concentration

Figure 3C:
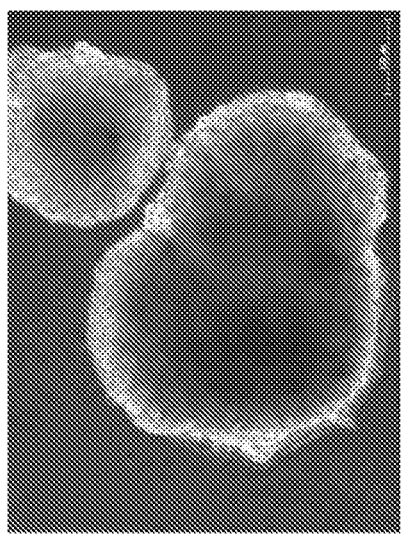
FIGS. 3A-3C are light photomicrographs of dithizone-stained fresh feline P3 ASCs.
Figure 3B:
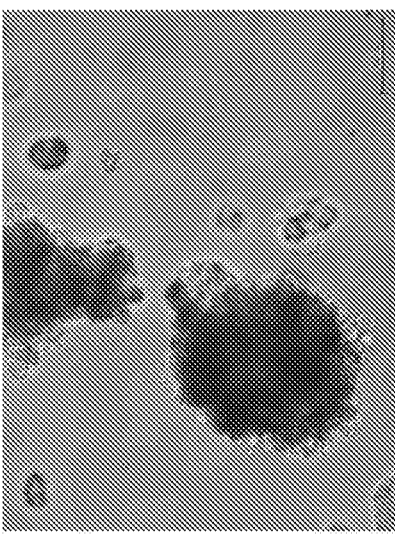
Figure 3A:
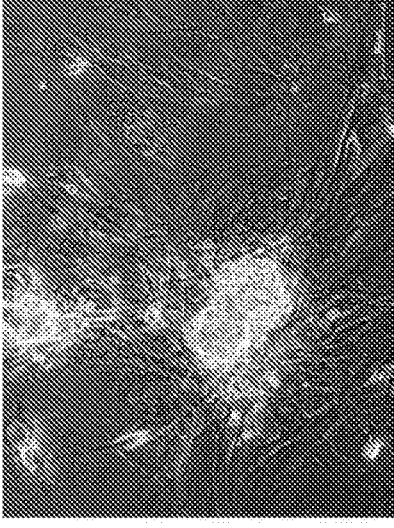

The cells cultured in induction medium formed clusters that stained dithizone (DTZ), confirming zinc accumulation (FIGS. 3B-3C), and those cultured in stromal medium did not stain with DTZ (FIG. 3A). As before, cells cultured in stromal medium attached to standard culture ware while those cultured in induction medium did not (FIG. 3A).

Example 5: Immunohistochemistry

Figure 4:
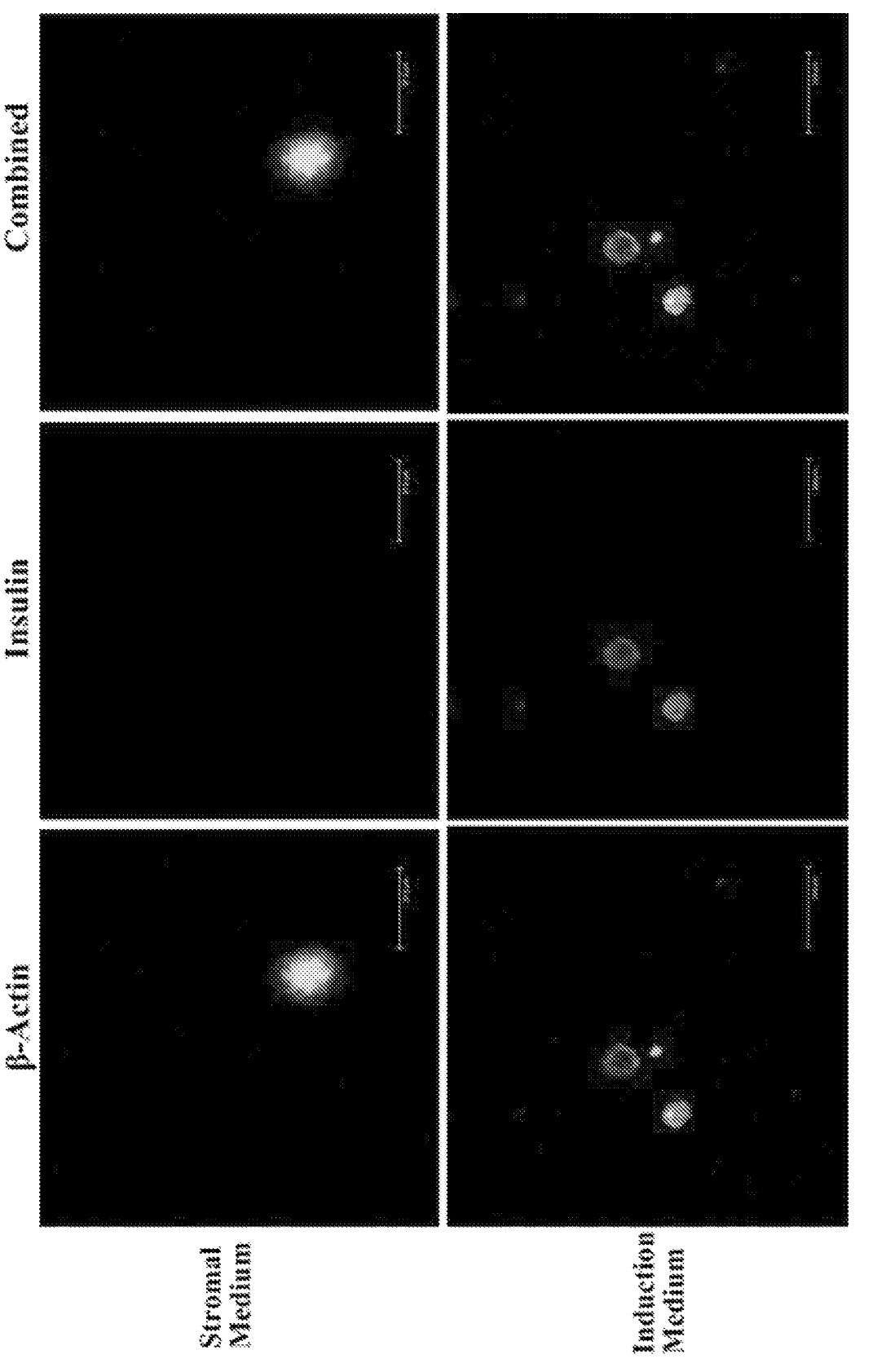
FIG. 4 illustrates fluorescent photomicrographs of cells cultured in stromal (top three panels) or induction medium (bottom three panels) and labeled with antibodies against insulin (middle two panels, red in the original) and actin (left two panels, blue in original). As illustrated, cells cultured in stromal media do not express insulin, but cells incubated in induction medium do express insulin.

The cells cultured in stromal medium lacked insulin expression, while the cells cultured in induction medium had strong insulin expression (FIG. 4).

Example 6: Glucose Challenge Assay

Figure 5:
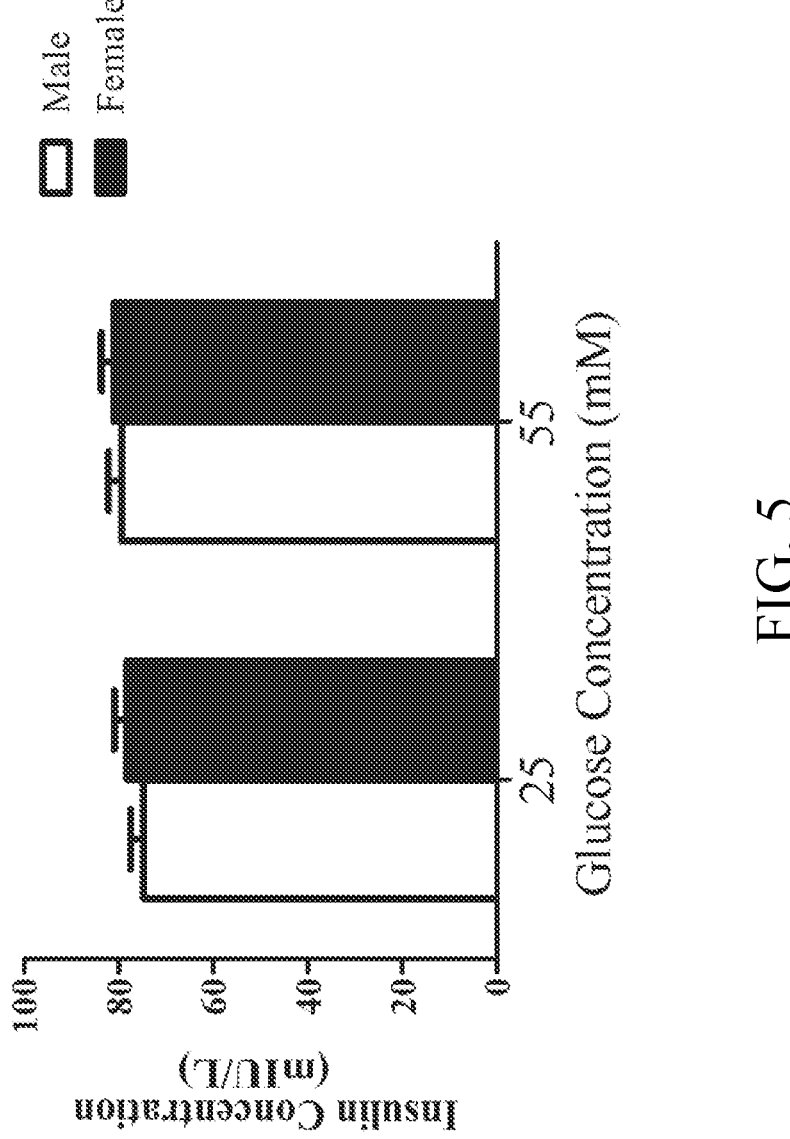
FIG. 5 graphically illustrates results of a glucose challenge assay of cells generated by the methods described herein. Insulin secretion from differentiated islet-like cell clusters exposed to distinct glucose concentrations in the medium. Columns with distinct superscripts are significantly different among differentiation stages within gender. Insulin secretion from differentiated islet-like cell clusters at stimulated concentrations of (25 and 55 mM) glucose are shown.

Male and female ASCs cultured in induction medium released insulin in response to glucose (FIG. 5). Insulin secretion was slightly higher (55.7 versus 62.7) at the higher glucose concentration. Insulin secretion was significantly higher at high glucose concentrations (25 and 55 mM) compared to a low glucose concentration (5.5 mM).

Example 7: Transmission Electron Microscopy—Ultrastructure

Figure 6B:
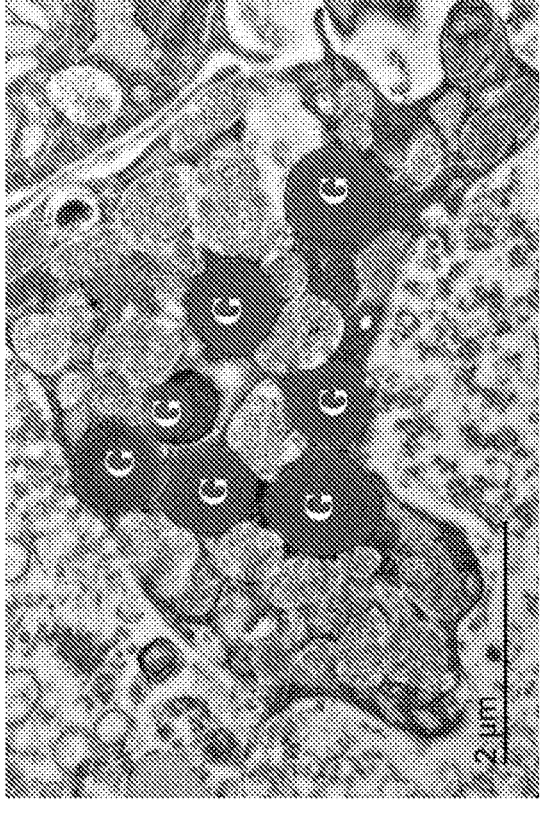
FIG. 6A-6B illustrate transmission electron photomicrographs of feline ASCs.
Figure 6A:
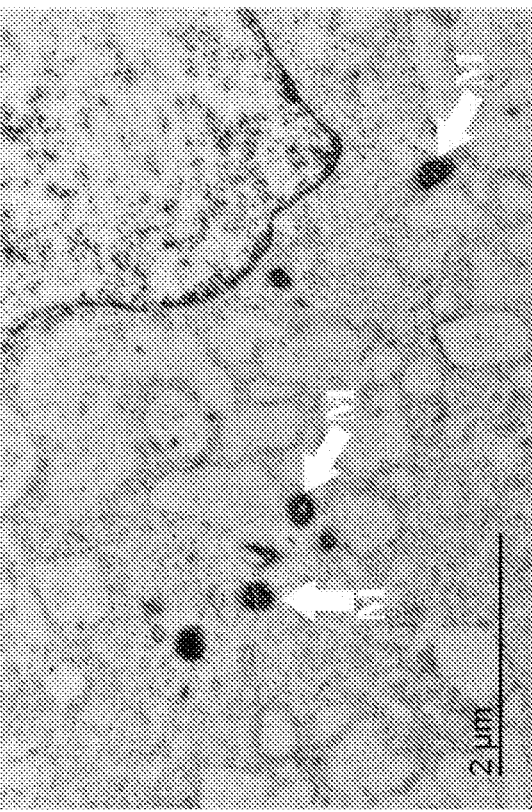

Cell ultrastructure was distinct between cells cultured in stromal versus induction medium. Notable differences were the presence abundant perinuclear mitochondria in the cells cultured in stromal medium (FIG. 6A) and secretory granules in the induced cells (FIG. 6B).

24

Example 8: Electroimmunohistochemistry—Insulin Localization

Figure 7B:
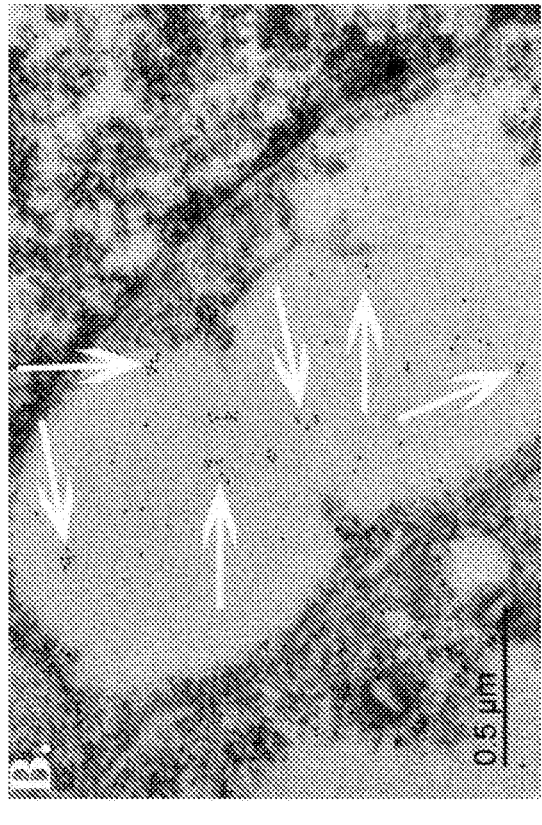
FIG. 7A-7B show transmission electron photomicrographs demonstrating insulin labeled with anti-insulin antibodies (arrows) in feline ASCs cultured in R pancreatic cell medium.
Figure 7A:
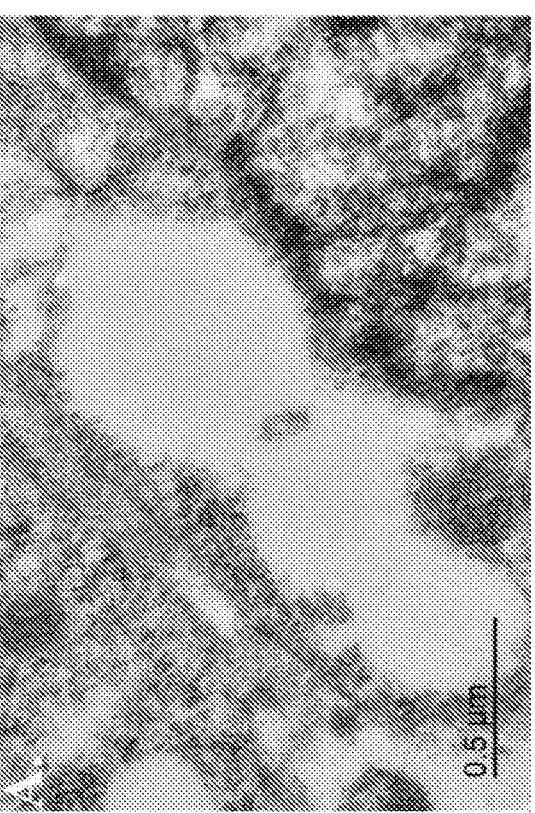

Insulin labeling was localized to the cytoplasm of cells cultured in induction medium, while there was no labeling in those cultured in stromal medium (FIG. 7).

Example 9: Scanning Electron Microscopy—Surface Ultrastructure

Figure 8B:
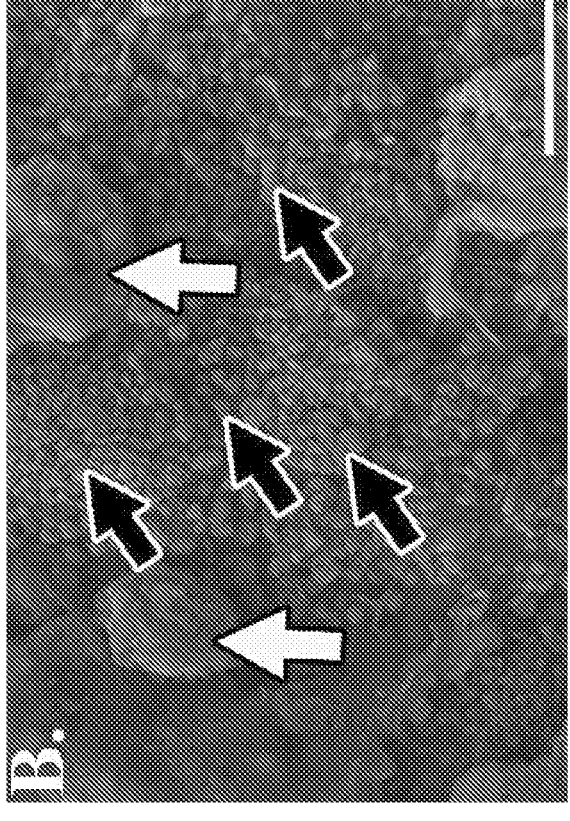
FIG. 8A-8B show scanning electron photomicrographs of feline ASCs.
Figure 8A:
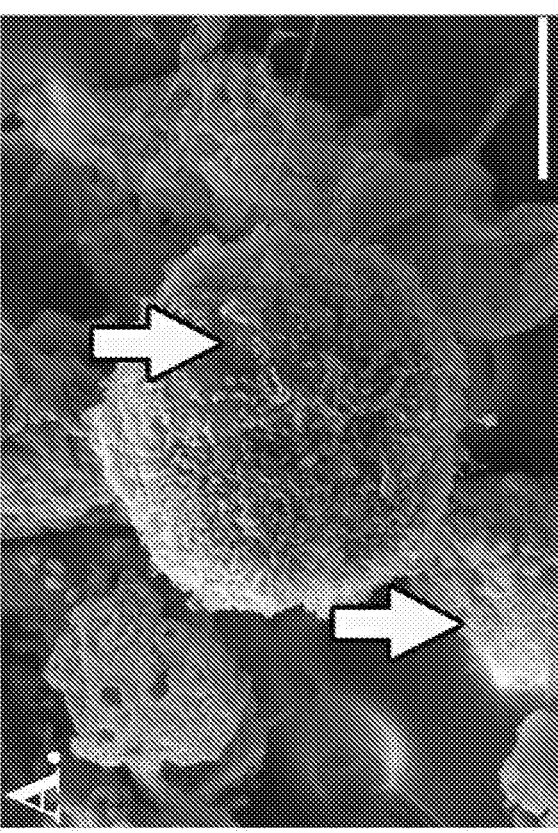

Cells cultured in stromal medium tended to form loose, spherical clusters while those in β cell induction medium formed larger, highly organized clusters with an irregular shape (FIG. 8). Proteinaceous material was apparent on the surface of differentiated cell clusters (FIG. 8B).

Example 10: Gene Expression

Figure 9A:
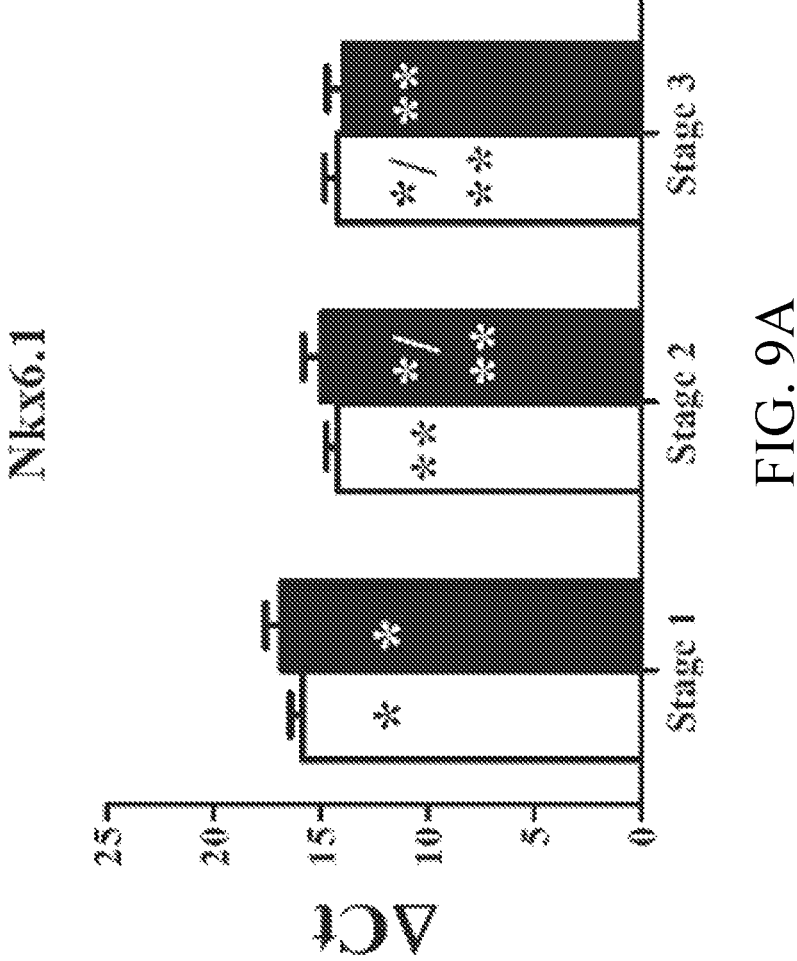
FIG. 9A-9D graphically illustrate expression of various feline genes in feline male (open bars) and female (dark bars) ASCs following three stages of pancreatic β cell culture induction.
Figure 9B:
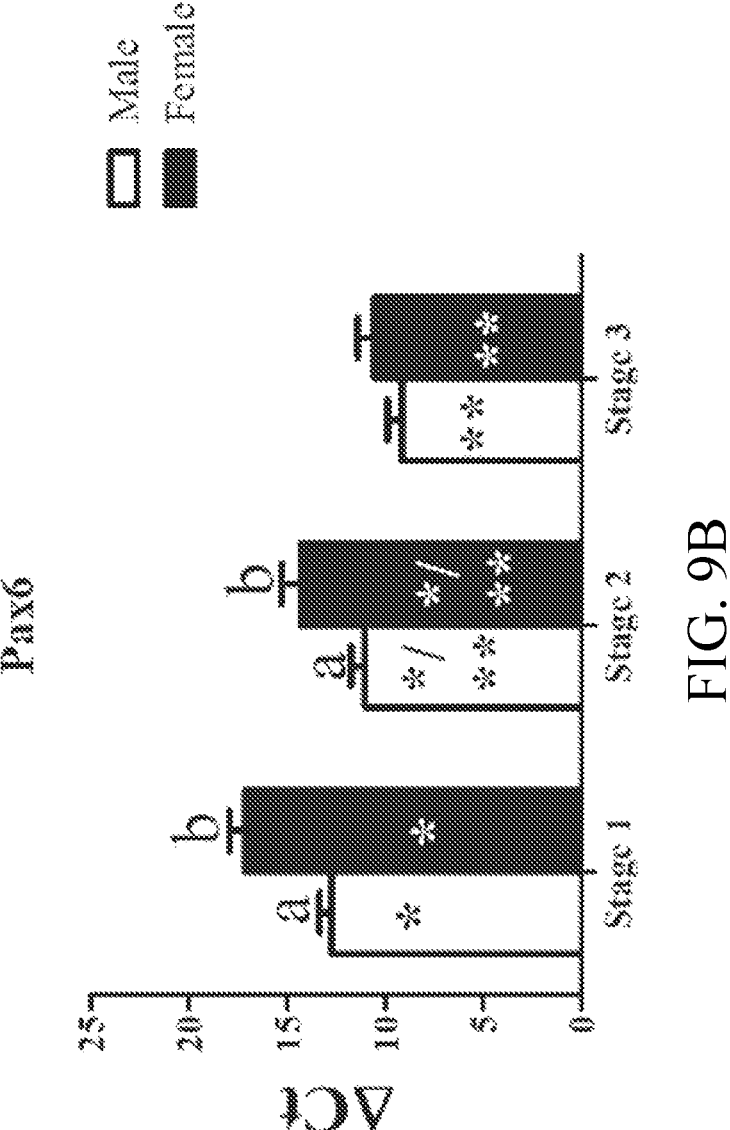
Figure 9C:
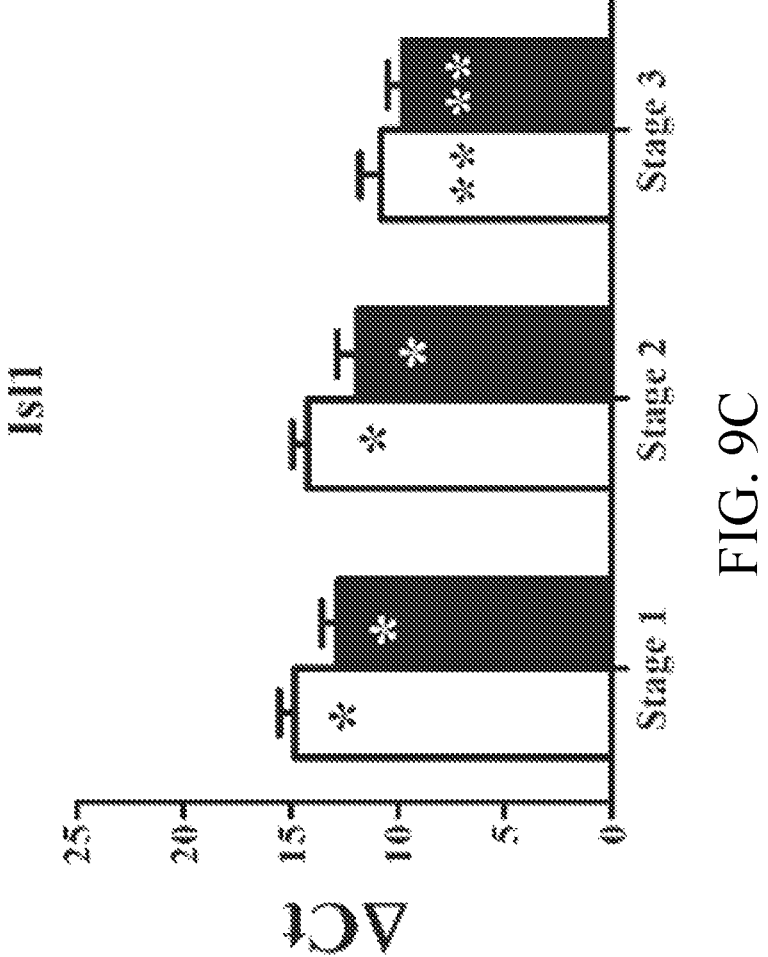
Figure 9D:
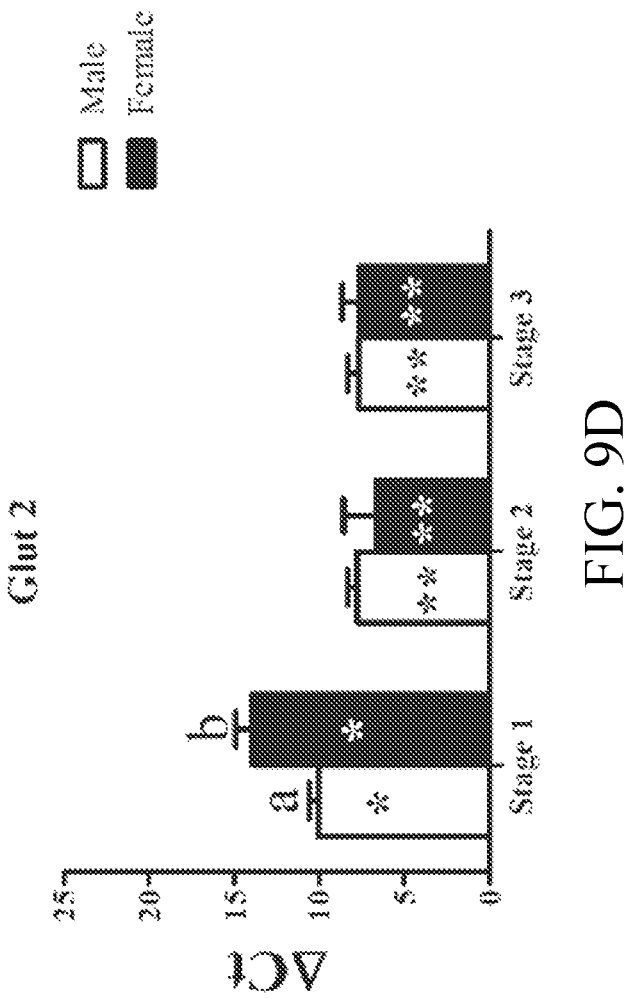
Figure 10A:
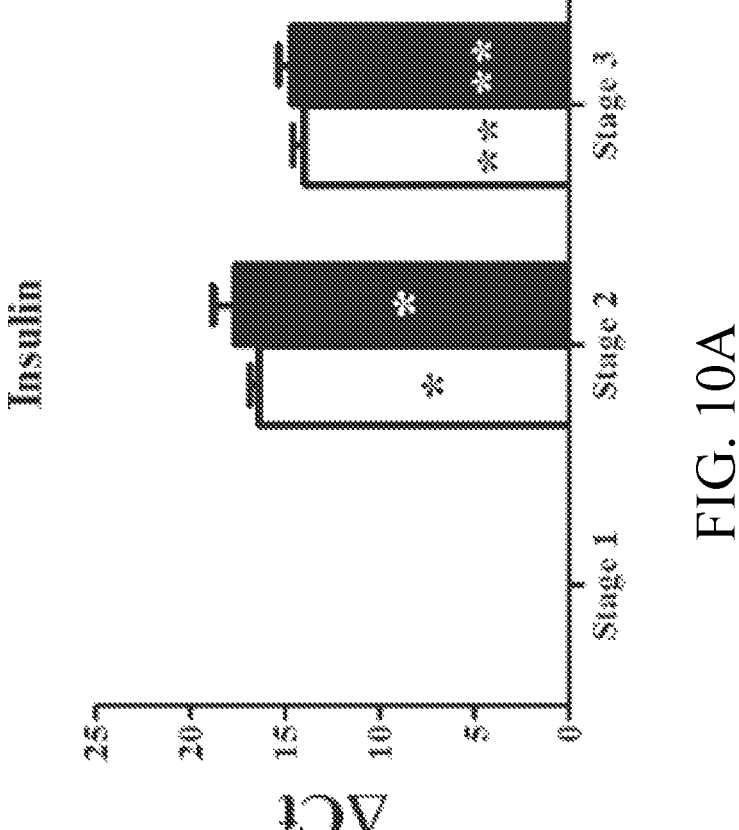
FIGS. 10A-10C graphically illustrate expression of various genes in feline male (open bars) and female (dark bars) ASCs following three stages of pancreatic β cell culture induction.
Figure 10B:
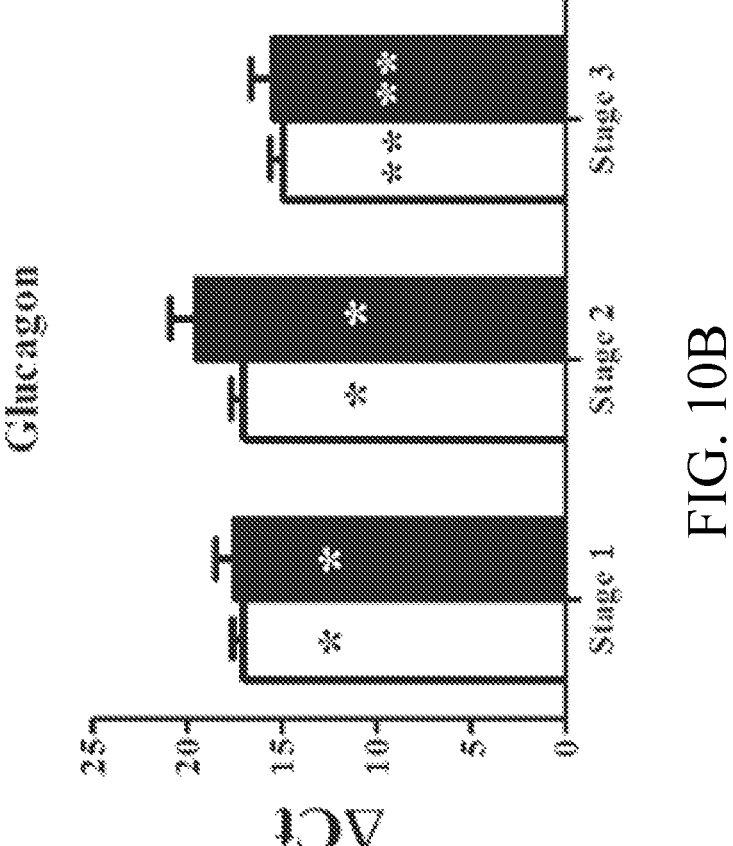
Figure 10C:
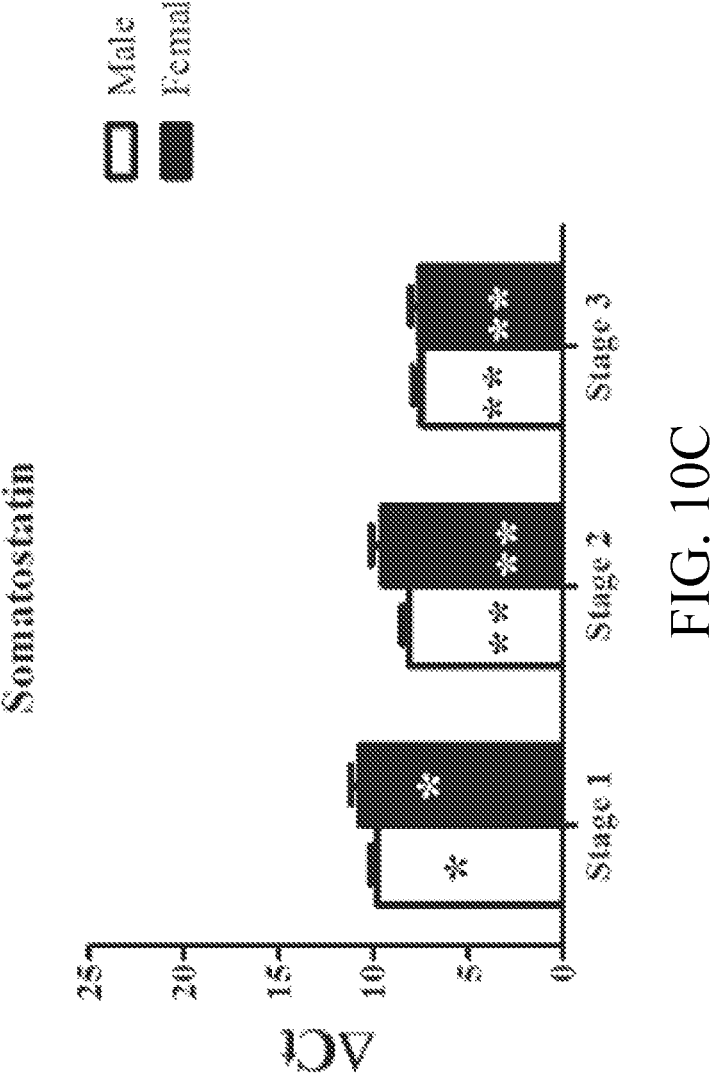
Figure 11A:
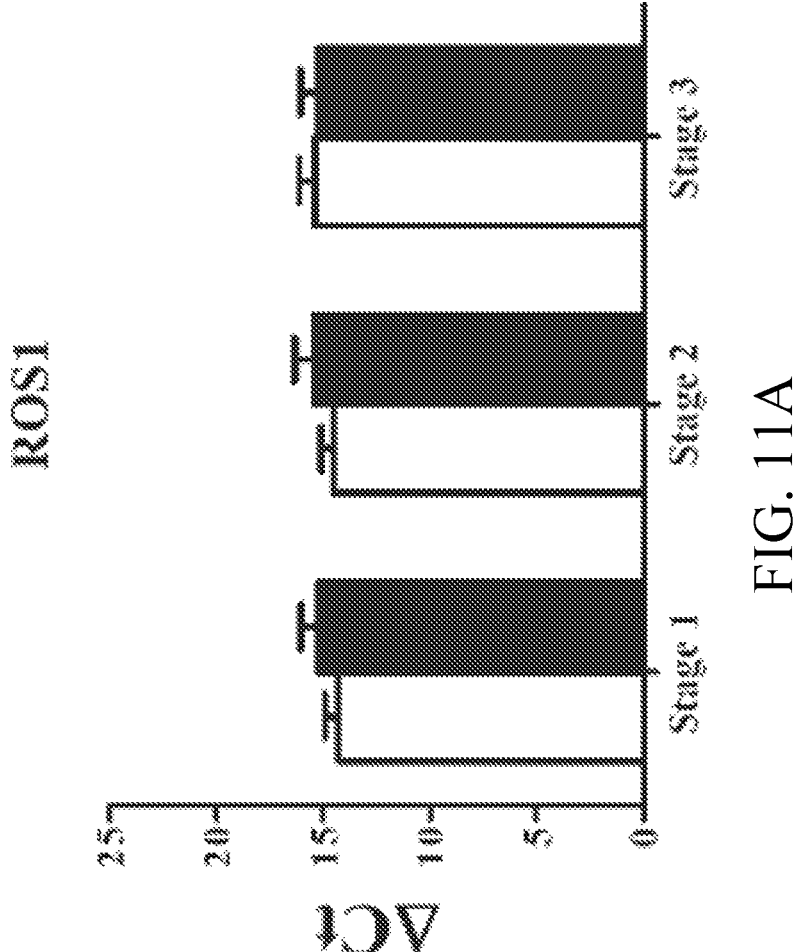
FIGS. 11A-11D graphically illustrate expression of various genes in feline male (open bars) and female (dark bars) ASCs following three stages of pancreatic β cell culture induction.
Figure 11B:
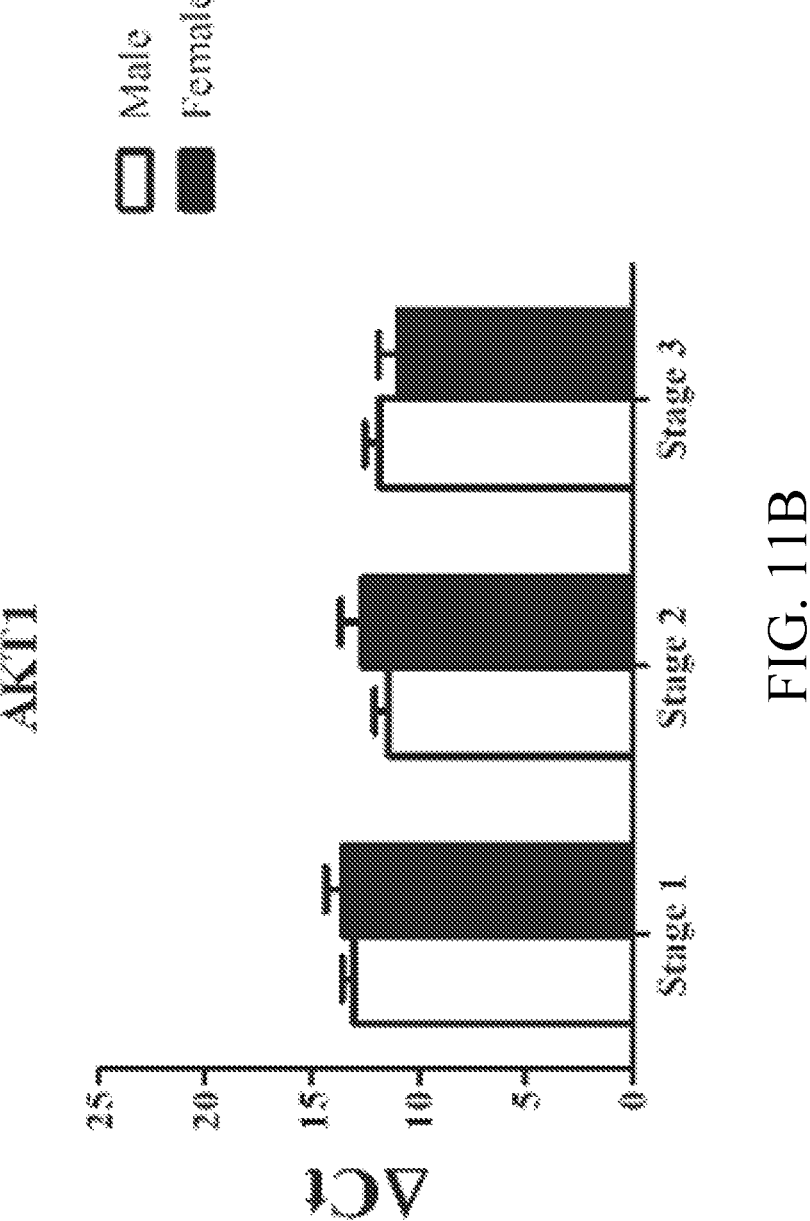
Figure 11C:
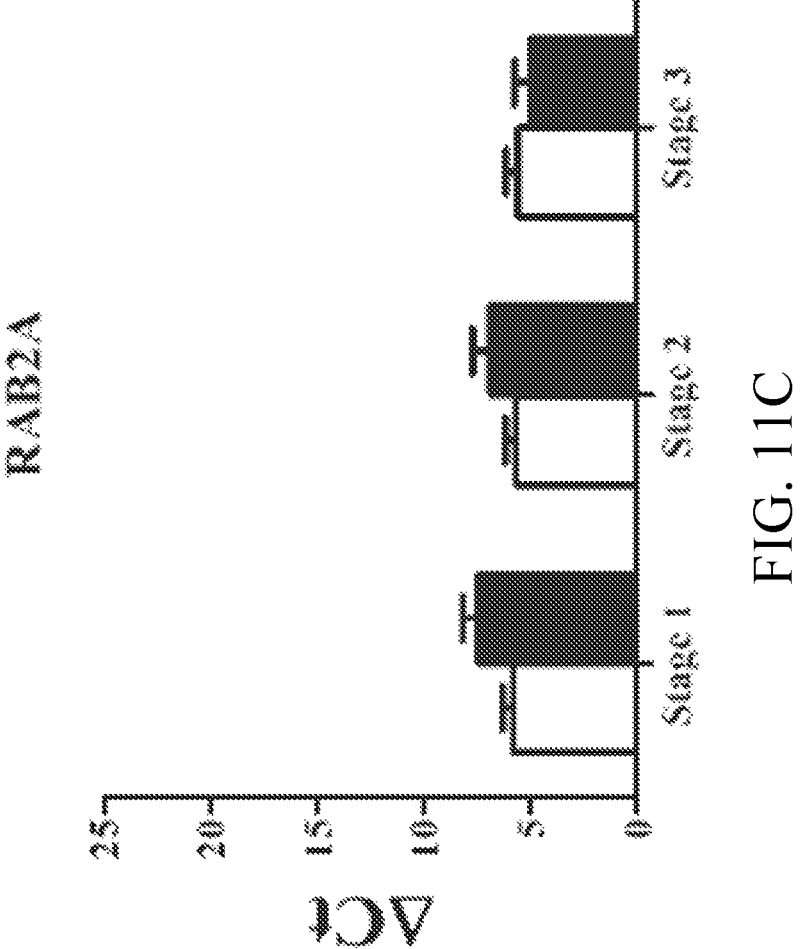
Figure 11D:
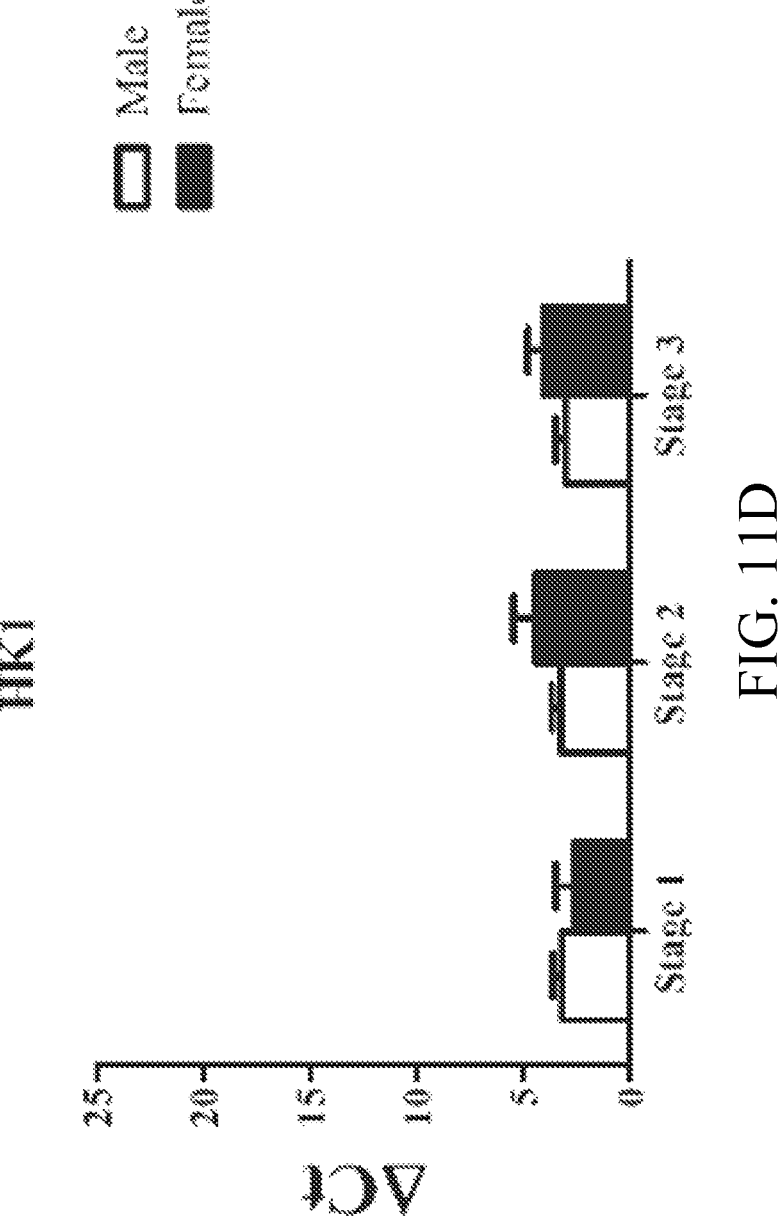
Figure 12:
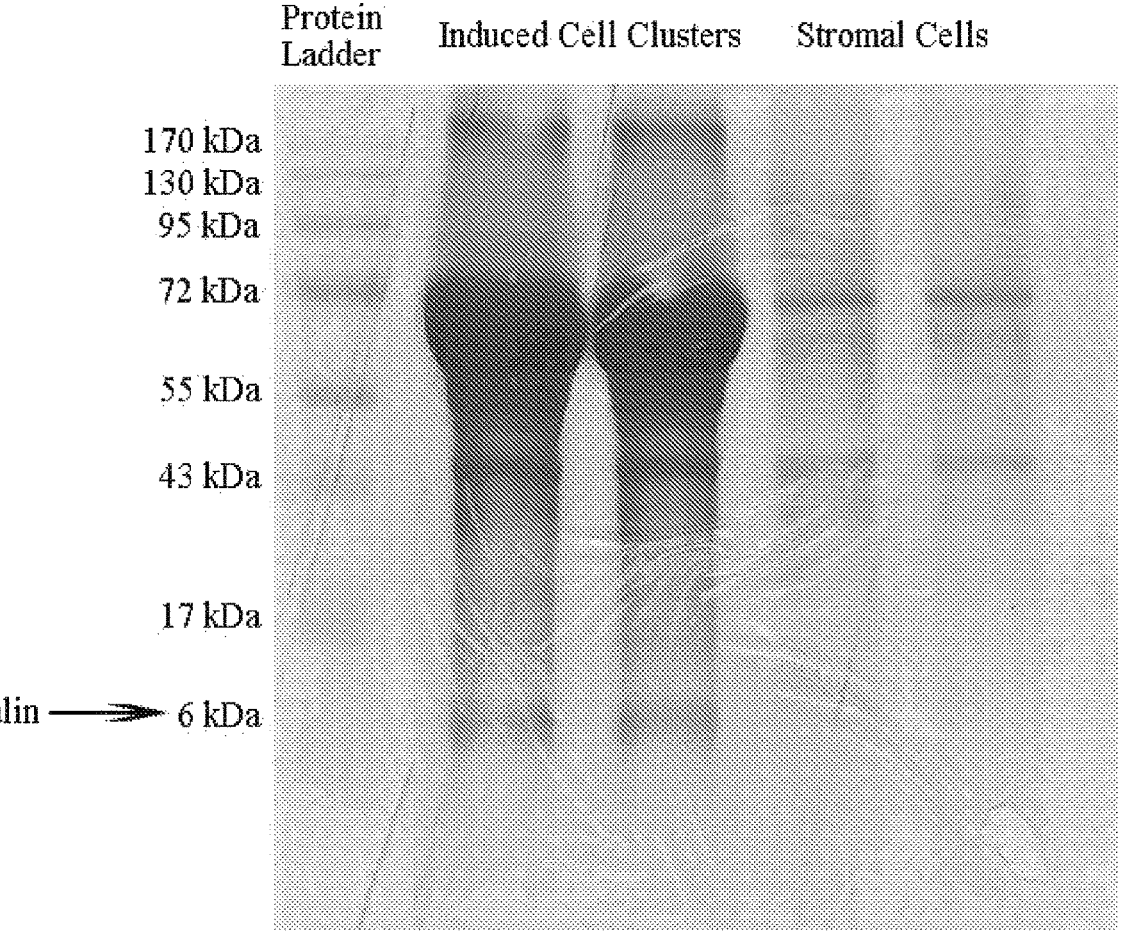
FIG. 12 shows an image of a western blot confirming insulin production by feline pancreatic cell clusters generated from adipose derived stem cells by the methods described herein. The blot shows the protein ladder left, two samples from cell clusters and two samples from paired samples cultured in stromal (basal) medium (left to right).

This Example illustrates expression patterns of cells at various stages of transdifferentiation.
Transcription Factor Expression
The mRNA levels of transcription factors (Nkx 6.1, Pax6, Isl1, and Glut-2) at Stage 1 tended to be lower than other induction stages (FIG. 9). The mRNA levels of Pax6 and Glut2 in female samples had lower expression than male at induction stages 1 and 2 and induction stage 1, respectively (FIGS. 9B and 9D).
Pancreatic β-Cell Target Gene Expression
Insulin expression detectable only after stage 2 and 3 induction (FIG. 10A). Glucagon expression was higher after stage 3 induction versus the other stages (FIG. 10B). Somatostatin levels were lower after stage 1 induction compared to the others (FIG. 10C).
Oncogene Expression
There was no difference in ROS1, AKT1, RAB2A, or HK1 expression among induction stages (FIG. 11).
Insulin Expression
As shown in FIG. 12, pancreatic cells generated via the methods described herein (stages 1-3) express insulin. In particular, FIG. 12 shows a Western blot demonstrating insulin protein produced by feline pancreatic beta cells generated from adipose derived stem cells. Columns from left to right: Protein ladder, pancreatic beta cell cluster, pancreatic beta cell cluster, adipose derived stem cells cultured in stromal medium, adipose derived stem cells cultured in stromal medium.

REFERENCES

1. Rand J S, Fleeman L M, Farrow H A, et al. *Canine and feline diabetes mellitus: nature or nurture? The Journal of nutrition* 2004; 134:2072S-20805.
2. Sittinger M, Hutmacher D W, Risbud M V. Current strategies for cell delivery in cartilage and bone regeneration. *Current opinion in biotechnology* 2004; 15:411-418.
3. Van der Valk J, Mellor D, Brands R, et al. The humane collection of fetal bovine serum and possibilities for serum-free cell and tissue culture. *Toxicology in vitro* 2004; 18:1-12.
4. Goossens M, Nelson R W, Feldman E C, et al. Response to insulin treatment and survival in 104 cats with diabetes mellitus (1985-1995). *Journal of Veterinary Internal Medicine* 1998; 12:1-6.
5. McCann T M, Simpson K E, Shaw D J, et al. Feline diabetes mellitus in the UK: the prevalence within an insured cat population and a questionnaire-based putative risk factor analysis. *Journal of Feline Medicine & Surgery* 2007; 9:289-299.

6. Panciera D, Thomas C, Eicker S, et al. Epizootiologic patterns of diabetes mellitus in cats: 333 cases (1980-1986). *Journal of the American Veterinary Medical Association* 1990; 197:1504-1508.

7. Prahl A, Guptill L, Glickman N W, et al. Time trends and risk factors for diabetes mellitus in cats presented to veterinary teaching hospitals. *Journal of Feline Medicine & Surgery* 2007; 9:351-358.

8. O'Brien T. Pathogenesis of feline diabetes mellitus. *Molecular and cellular endocrinology* 2002; 197:213-219.

9. Schwartz A. Diabetes mellitus: does it affect bone? *Calcified Tissue International* 2003; 73:515-519.

10. Shehadeh A, Regan T J. Cardiac consequences of diabetes mellitus. *Clinical cardiology* 1995; 18:301-305.

11. Mizisin A P, Shelton G D, Burgers M L, et al. Neurological complications associated with spontaneously occurring feline diabetes mellitus. *Journal of Neuropathology & Experimental Neurology* 2002; 61:872-884.

12. Fu Z, Gilbert E R, Liu D. Regulation of insulin synthesis and secretion and pancreatic Beta-cell dysfunction in diabetes. *Current diabetes reviews* 2013; 9:25.

13. Betsholtz C, Christmanson L, Engström U, et al. Structure of cat islet amyloid polypeptide and identification of amino acid residues of potential significance for islet amyloid formation. *Diabetes* 1990; 39:118-122.

14. Chance R E, Ellis R M, Bromer W W. Porcine proinsulin: characterization and amino acid sequence. *Science* 1968; 161:165-167.

15. Zhang N, Dietrich M A, Lopez M J. Therapeutic doses of multipotent stromal cells from minimal adipose tissue. *Stem Cell Reviews and Reports* 2014; 10:600-611.

16. Kono S, Kazama T, Kano K, et al. Phenotypic and functional properties of feline dedifferentiated fat cells and adipose-derived stem cells. *The Veterinary Journal* 2014; 199:88-96.

17. Webb T L, Quimby J M, Dow S W. In vitro comparison of feline bone marrow-derived and adipose tissue-derived mesenchymal stem cells. *Journal of feline medicine and surgery* 2012; 14:165-168.

18. Moshtagh P R, Emami S H, Sharifi A M. Differentiation of human adipose-derived mesenchymal stem cell into insulin-producing cells: an in vitro study. *Journal of physiology and biochemistry* 2013; 69:451-458.

19. Buang M L M, Seng H K, Chung L H, et al. In vitro generation of functional insulin-producing cells from lipoaspirated human adipose tissue-derived stem cells. *Archives of medical research* 2012; 43:83-88.

20. Dave S, Vanikar A, Trivedi H. Extrinsic factors promoting in vitro differentiation of insulin-secreting cells from human adipose tissue-derived mesenchymal stem cells. *Applied biochemistry and biotechnology* 2013; 170:962-971.

21. Dubey A, Malik H, Singhal D, et al. 198 isolation, characterization, and in vitro differentiation of goat adipose-tissue-derived mesenchymal stem cells into pancreatic islets-like cells. *Reproduction, Fertility and Development* 2014; 26:213-213.

22. Chen C-Z, Li L, Lodish H F, et al. MicroRNAs modulate hematopoietic lineage differentiation. *science* 2004; 303: 83-86.

23. Chen L-B, Jiang X-B, Yang L. Differentiation of rat marrow mesenchymal stem cells into pancreatic islet beta-cells. *World Journal of Gastroenterology* 2004; 10:3016-3020.

24. Shapiro A J, Lakey J R, Ryan E A, et al. Islet transplantation in seven patients with type 1 diabetes mellitus using a glucocorticoid-free immunosuppressive regimen. *New England Journal of Medicine* 2000; 343:230-238.

25. Ryan E A, Paty B W, Senior P A, et al. Five-year follow-up after clinical islet transplantation. *Diabetes* 2005; 54:2060-2069.

26. D'Amour K A, Bang A G, Eliazer S, et al. Production of pancreatic hormone-expressing endocrine cells from human embryonic stem cells. *Nature biotechnology* 2006; 24:1392.

27. Dang L T-T, Bui A N-T, Pham V M, et al. Production of islet-like insulin-producing cell clusters in vitro from adipose-derived stem cells. *Biomedical Research and Therapy* 2015; 2:184-192.

28. Chandra V, Phadnis S, Nair P D, et al. Generation of pancreatic hormone-expressing islet-like cell aggregates from murine adipose tissue-derived stem cells. *Stem Cells* 2009; 27:1941-1953.

29. Evans J L, Goldfine I D, Maddux B A, et al. Are oxidative stress-activated signaling pathways mediators of insulin resistance and β-cell dysfunction? *Diabetes* 2003; 52:1-8.

30. Okura H, Komoda H, Fumimoto Y, et al. Transdifferentiation of human adipose tissue-derived stromal cells into insulin-producing clusters. *Journal of Artificial Organs* 2009; 12:123-130.

31. Lopez M, Jarazo J. State of the art: stem cells in equine regenerative medicine. *Equine veterinary journal* 2015; 47:145-154.

32. Liu Y, Xu X, Ma X, et al. Cryopreservation of human bone marrow-derived mesenchymal stem cells with reduced dimethylsulfoxide and well-defined freezing solutions. *Biotechnology progress* 2010; 26:1635-1643.

33. Pokrywczynska M, Krzyzanowska S, Jundzill A, et al. Differentiation of stem cells into insulin-producing cells: current status and challenges. *Archivum immunologiae et therapiae experimentalis* 2013; 61:149-158.

34. Janjic D, Wollheim C B. Effect of 2-mercaptoethanol on glutathione levels, cystine uptake and insulin secretion in insulin-secreting cells. *European Journal of Biochemistry* 1992; 210:297-304.

35. Dominici M, Le Blanc K, Mueller I, et al. Minimal criteria for defining multipotent mesenchymal stromal cells. The International Society for Cellular Therapy position statement. *Cytotherapy* 2006; 8.

36. Vaca P, Berna G, Martin F, et al. Nicotinamide induces both proliferation and differentiation of embryonic stem cells into insulin-producing cells. Transplantation proceedings 2003; 2021-2023.

37. Polak M, Bouchareb-Banaei L, Scharfmann R, et al. Early pattern of differentiation in the human pancreas. *Diabetes* 2000; 49:225-232.

38. Aksu A E, Rubin J P, Dudas J R, et al. Role of gender and anatomical region on induction of osteogenic differentiation of human adipose-derived stem cells. *Annals of plastic surgery* 2008; 60:306-322.

39. Sander M, NeubUser A, Kalamaras J, et al. Genetic analysis reveals that PAX6 is required for normal transcription of pancreatic hormone genes and islet development. *Genes & development* 1997; 11:1662-1673.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements are intended to describe and summarize various embodiments of the invention according to the foregoing description in the specification.

Statements:

1) A method comprising:
   a. Stage 1: culturing adult adipose-derived multipotent stromal (stem) cells (ASCs) for about 1-4 days in a first culture medium comprising insulin-transferrin-selenium, a TGFβ family member (e.g., activin A), an HDAC inhibitor (e.g., sodium butyrate), and 2-mercapethanol to generate a first population of cells that express at least one of the following genes: Nkx 6.1, Pax6, Isl1, or Glut-2;
   b. Stage 2: culturing the first population of cells for 4 to 8 days in a second culture medium comprising insulin-transferrin-selenium, and taurine to generate a second population of cells; and
   c. Stage 3: culturing the second population of cells for 2 to 6 days in a third culture medium comprising insulin-transferrin-selenium, taurine, glucagon-like peptide 1 (GLP-1), nicotinamide, pentagastrin, and betacellulin to generate a third population of cells.

2) The method of statement 1, wherein the first culture medium, the second culture medium, and the third culture medium further comprise at least one, at least two, at least three, or at least four of the following: basic fibroblast growth factor (bFGF), hepatocyte growth factor (HGF), laminin, N-2 supplement, or B-27 supplement.

3) The method of statement 1 or 2, wherein the first culture medium, the second culture medium, and the third culture medium further comprise glucose, serum albumin (e.g., bovine serum albumin).

4) The method of statement 1, 2, or 3, wherein the third culture medium further comprises theophylline.

5) The method of statement 1-3, or 4, where the second population of cells and/or the third population of cells express insulin.

6) The method of statement 1-4 or 5, where cells in the first population of cells do not express detectable amounts of insulin mRNA as detected by quantitative polymerase chain polymerase reaction.

7) The method of statement 1-5 or 6, further comprising administering the third population of cells, or a portion thereof, to a mammalian subject.

8) The method of statement 1-6 or 7, further comprising administering the third population of cells, or a portion thereof, to a feline subject.

9) The method of statement 1-7 or 8, wherein the adult adipose-derived multipotent stromal (stem) cells (ASCs) are cultured on an ultra-low attachment culture plate.

10) The method of statement 1-8 or 9, wherein cells in the first population are cultured on an ultra-low attachment culture plate.

11) The method of statement 1-9 or 10, wherein cells in the first population are cultured on culture plates or in culture vessels coated with protein.

12) The method of statement 1-10 or 11, wherein cells in the second population expresses higher or lower levels of at least one of the following genes: Nkx 6.1, Pax6, Isl1, or Glut-2 than cells in the first population of cells.

13) The method of statement 1-11 or 12, further comprising culturing cells from the third population and isolating insulin.

14) The method of statement 13, wherein the insulin is isolated from the cultured cells.

15) The method of statement 13 or 14, wherein the insulin is isolated from the culture medium.

16) A composition comprising a first population of cells made by culturing adult adipose-derived multipotent stromal (stem) cells (ASCs) from feline adipose tissue for about 1-4 days in a first culture medium comprising insulin-transferrin-selenium, a TGFβ family member (e.g., activin A), an HDAC inhibitor (e.g., sodium butyrate), and 2-mercapethanol to generate a first population of cells that express at least one of the following genes: Nkx 6.1, Pax6, Isl1, or Glut-2.

17) The composition of statement 16, wherein the adult adipose-derived multipotent stromal (stem) cells (ASCs) are cultured on an ultra-low attachment culture plate.

18) A composition comprising a second population of cells made by:
   a. Stage 1: culturing adult adipose-derived multipotent stromal (stem) cells (ASCs) from feline adipose tissue for about 1-4 days in a first culture medium comprising insulin-transferrin-selenium, a TGFβ family member (e.g., activin A), an HDAC inhibitor (e.g., sodium butyrate), and 2-mercapethanol to generate a first population of cells that express at least one of the following genes: Nkx 6.1, Pax6, Isl1, or Glut-2; and
   b. Stage 2: culturing the first population of cells for 4 to 8 days in a second culture medium comprising insulin-transferrin-selenium, and taurine to generate a second population of cells.

19) The composition of statement 18, wherein the adult adipose-derived multipotent stromal (stem) cells (ASCs) and/or cells in the first population are cultured on an ultra-low attachment culture plate.

20) The composition of statement 16-17 or 18, wherein cells in the second population express higher or lower levels of at least one of the following genes: Nkx 6.1, Pax6, Isl1, or Glut-2 than cells in the first population of cells.

21) A composition comprising a third population of cells made by:
   a. Stage 1: culturing adult adipose-derived multipotent stromal (stem) cells (ASCs) from feline adipose tissue for about 1-4 days in a first culture medium comprising insulin-transferrin-selenium, a TGFβ family member (e.g., activin A), an HDAC inhibitor (e.g., sodium butyrate), and 2-mercapethanol to generate a first population of cells that express at least one of the following genes: Nkx 6.1, Pax6, Isl1, or Glut-2;
   b. Stage 2: culturing the first population of cells for 4 to 8 days in a second culture medium comprising insulin-transferrin-selenium, and taurine to generate a second population of cells; and
   c. Stage 3: culturing the second population of cells for 2 to 6 days in a third culture medium comprising insulin-transferrin-selenium, taurine, glucagon-like peptide 1 (GLP-1), nicotinamide, pentagastrin, and betacellulin to generate a third population of cells.

22) The composition of statement 21, wherein the adult adipose-derived multipotent stromal (stem) cells (ASCs), and/or cells in the first population are cultured on an ultra-low attachment culture plate.

23) A composition comprising at least four, or at least five, or at least six, or at least seven, or at least eight, or at least nine, or at least ten of the following: glucose, bovine serum albumin, insulin-transferrin-selenium, a TGFβ family member (e.g., activin A), an HDAC inhibitor (e.g., sodium butyrate), 2-mercapethanol, N-2 supplement, B-27 supplement, laminin, mammalian hepatocyte growth factor (HGF), or basic fibroblast growth factor (bFGF).

24) A composition comprising at least four, or at least five, or at least six, or at least seven, or at least eight of the following: glucose, bovine serum albumin, insulin-transferrin-selenium, taurine, laminin, basic fibroblast growth factor (bFGF), N-2 supplement, B-27 supplement, or mammalian hepatocyte growth factor (HGF).

25) A composition comprising at least four, or at least five, or at least six, or at least seven, or at least eight, or at least nine, or at least ten, or at least eleven, or at least twelve of the following: glucose, bovine serum albumin, insulin-transferrin-selenium, taurine, glucagon-like peptide 1 (GLP-1), nicotinamide, non-essential amino acids, pentagastrin, N-2 supplement, B-27 supplement, human hepatocyte growth factor (HGF), basic fibroblast growth factor (bFGF), laminin, or betacellulin.

26) The composition of statement 23, 24, or 25, which is formulated as a culture medium.

The specific compositions, constructs, and methods described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

What is claimed:
1. A cell culture derived from a population of adult feline adipose multipotent stromal cells (ASCs), comprising:
    a mixed population of pancreatic hormone-expressing islet-like cells that comprises pancreatic precursor cells, insulin-producing cells, pancreatic cells or a combination thereof; and
    a culture medium comprising an effective amount of insulin-transferrin-selenium, taurine, glucagon-like peptide 1 (GLP-1), nicotinamide, pentagastrin, and betacellulin, mammalian hepatocyte growth factor (HGF), basic fibroblast growth factor (bFGF), and at least one component selected from the group consisting of glucose, bovine serum albumin, non-essential amino acids, N-2 supplement, a neuron-induction culture supplement,
    wherein the culture medium further comprises an effective amount of laminin to generate the mixed population of pancreatic hormone-expressing islet-like cells that can express insulin in response to a glucose stimulus in a dose dependent manner and can express glucagon and somatostatin.
2. The cell culture of claim 1, wherein the mixed population of pancreatic hormone-expressing islet-like cells forms organized clusters of irregular shape.
3. The cell culture of claim 2, wherein the organized clusters comprise proteinaceous material on the cell surfaces.
4. The cell culture of claim 1, wherein the mixed population of pancreatic hormone-expressing islet-like cells express at least one marker selected from the group consisting of Nkx 6.1, Pax6, Isl1, and Glut-2.
5. The cell culture of claim 1, wherein the population of pancreatic precursor cells, insulin-producing cells, pancreatic cells, or a combination thereof is isolated from the mixed population of pancreatic hormone-expressing islet-like cells by:

co-culturing said mixed population of pancreatic hormone-expressing islet-like cells with a binding reagent targeting a marker expressed by said population of pancreatic precursor cells, insulin-producing cells and/or pancreatic cells to produce a population of reagent-bound cells, wherein said marker which is not substantially expressed in a population of non-reagent-bound cells is present among said mixed population of pancreatic hormone-expressing islet-like cells,
    subsequently separating said population of reagent-bound cells from said population of non-reagent-bound-cells, and,
    optionally further plating said population of reagent-bound cells on a surface coated with laminin in an expansion medium comprising a serum concentration ranging from 0 to 20% (v/v).
6. The cell culture of claim 1, wherein the mixed population of pancreatic hormone-expressing islet-like cells are derived from the population of ASCs by a transdifferentiation method comprising:
    a first stage wherein the population of ASCs differentiates into endoderm cell clusters that can express Nkx 6.1, Pax6, Isl1, and Glut-2, and
    a second stage wherein the endoderm cell clusters differentiate into a mixed population of cells of pancreatic endodermal lineage that can express insulin, and a third stage wherein the mixed population of cells of pancreatic endodermal lineage differentiates into a mixed population of pancreatic hormones-expressing islet-like cells that can express insulin in response to a glucose stimulus in a dose dependent manner and can express glucagon and somatostatin; and
wherein, at each stage, the population of cells are cultured in a culture medium supplemented with laminin.

* * * * *